(12) United States Patent
Rust et al.

(10) Patent No.: US 10,140,422 B2
(45) Date of Patent: Nov. 27, 2018

(54) PROGRESSION ANALYTICS SYSTEM

(71) Applicant: BATTELLE MEMORIAL INSTITUTE, Columbus, OH (US)

(72) Inventors: Steven W. Rust, Worthington, OH (US); Daniel Haber, Columbus, OH (US)

(73) Assignee: Battelle Memorial Institute, Columbus, OH (US)

( * ) Notice: Subject to any disclaimer, the term of this patent is extended or adjusted under 35 U.S.C. 154(b) by 452 days.

(21) Appl. No.: 14/853,377

(22) Filed: Sep. 14, 2015

(65) Prior Publication Data
US 2016/0004840 A1 Jan. 7, 2016

Related U.S. Application Data

(63) Continuation of application No. PCT/US2014/030514, filed on Mar. 17, 2014.
(Continued)

(51) Int. Cl.
G16H 50/00 (2018.01)
G06F 19/00 (2018.01)
(Continued)

(52) U.S. Cl.
CPC .......... G06F 19/3443 (2013.01); G06F 19/00 (2013.01); G06Q 50/22 (2013.01); G16H 50/70 (2018.01)

(58) Field of Classification Search
CPC .... G06Q 50/22; G06Q 50/24; G06F 19/3437; G06F 19/3443; G06H 50/70
See application file for complete search history.

(56) References Cited

U.S. PATENT DOCUMENTS 6,110,109 A 8/2000 Hu et al.
6,409,664 B1 6/2002 Kattan et al.
(Continued)

FOREIGN PATENT DOCUMENTS

JP 2006501534 T 1/2006
WO 00/65418 A2 11/2000
(Continued)

OTHER PUBLICATIONS

Thomas, Shane; Notification of Transmittal of the International Search Report and the Written Opinion of the International Searching Authority for PCT Application No. PCT/US2014/030514, dated Aug. 28, 2014; International Search Authority/US; Commissioner for Patents; Alexandria, Virginia.
(Continued)

Primary Examiner — Joseph D Burgess
(74) Attorney, Agent, or Firm — Thomas E. Lees, LLC

(57) ABSTRACT

A method of identifying insights related to the occurrence of an adverse health outcome of interest, comprises extracting electronic clinical data associated with historical healthcare encounters. The method also comprises defining patient groups based upon similar data patterns present in the extracted electronic clinical data wherein the patient groups have varying likelihood for the adverse health outcome. Still further, the method comprises deriving hypothesized etiological explanations for why one or more patient groups have higher likelihood when compared to other patient groups. Optionally, the method comprises identifying clinical interventions that are intended to reduce the likelihood of the adverse outcome for certain patient groups.

23 Claims, 8 Drawing Sheets

Related U.S. Application Data

(60) Provisional application No. 61/789,695, filed on Mar. 15, 2013.

(51) Int. Cl.
*G06Q 50/22* (2018.01)
*G16H 50/70* (2018.01)

(56) References Cited

U.S. PATENT DOCUMENTS

| | | |
|---|---|---|
| 6,533,724 B2 | 3/2003 | McNair |
| 7,181,375 B2 | 2/2007 | Rao et al. |
| 7,213,009 B2 | 5/2007 | Pestotnik et al. |
| 7,230,529 B2 | 6/2007 | Ketcherside, Jr. et al. |
| 7,324,928 B2 | 1/2008 | Kitchen et al. |
| 7,392,140 B2 | 6/2008 | Serena et al. |
| 7,447,643 B1 | 11/2008 | Olson et al. |
| 7,617,078 B2 | 11/2009 | Rao et al. |
| 7,634,360 B2 | 12/2009 | Davalos et al. |
| 7,716,068 B2 | 5/2010 | Ball et al. |
| 7,734,656 B2 | 6/2010 | Bessette et al. |
| 7,801,591 B1 | 9/2010 | Shusterman |
| 7,840,512 B2 | 11/2010 | Pandya et al. |
| 7,853,456 B2 | 12/2010 | Soto et al. |
| 7,856,456 B2 | 12/2010 | Bessette |
| 7,912,734 B2 | 3/2011 | Kil |
| 7,984,079 B2 | 7/2011 | Bessette |
| 8,034,799 B2 | 10/2011 | Cooper et al. |
| 8,041,417 B2 | 10/2011 | Jonckheere et al. |
| 8,229,881 B2 | 7/2012 | Pedro et al. |
| 8,265,955 B2 * | 9/2012 | Michelson ............... G06F 19/24 705/2 |
| 8,494,871 B2 | 7/2013 | Schaffer et al. |
| 8,540,515 B2 | 9/2013 | Williams et al. |
| 2002/0186818 A1 | 12/2002 | Arnaud et al. |
| 2002/0193667 A1 | 12/2002 | McNair |
| 2003/0220777 A1 | 11/2003 | Kitchen et al. |
| 2005/0181386 A1 | 8/2005 | Diamond et al. |
| 2006/0025931 A1 | 2/2006 | Rosen et al. |
| 2006/0052945 A1 | 3/2006 | Rabinowitz et al. |
| 2006/0173663 A1 * | 8/2006 | Langheier ............ G06F 19/3437 703/11 |
| 2006/0253262 A1 | 11/2006 | Ching et al. |
| 2007/0122347 A1 | 5/2007 | Statnikov et al. |
| 2007/0244375 A1 | 10/2007 | Jenkins et al. |
| 2008/0097794 A1 | 4/2008 | Arnaud et al. |
| 2008/0133275 A1 | 6/2008 | Haug et al. |
| 2008/0140371 A1 | 6/2008 | Warner |
| 2008/0306763 A1 * | 12/2008 | James ................. G06F 19/3418 705/2 |
| 2009/0006061 A1 | 1/2009 | Thukral et al. |
| 2009/0012715 A1 | 1/2009 | Goldfarb-Rumyantzev |
| 2009/0024615 A1 | 1/2009 | Pedro et al. |
| 2009/0075271 A1 | 3/2009 | Schwinn et al. |
| 2009/0177495 A1 | 7/2009 | Abousy et al. |
| 2009/0187427 A1 | 7/2009 | Durand |
| 2009/0197287 A1 | 8/2009 | Hu et al. |
| 2009/0259487 A1 | 10/2009 | Rao et al. |
| 2009/0276287 A1 | 11/2009 | Firouzbakht et al. |
| 2009/0299154 A1 | 12/2009 | Segman |
| 2010/0036192 A1 | 2/2010 | Yao et al. |
| 2010/0114599 A1 | 5/2010 | Lanning et al. |
| 2010/0174152 A1 | 7/2010 | McNair |
| 2010/0179765 A1 | 7/2010 | Ching et al. |
| 2010/0285082 A1 | 11/2010 | Fernandez |
| 2010/0332254 A1 | 12/2010 | Maschke et al. |
| 2011/0055141 A1 | 3/2011 | Jamil et al. |
| 2011/0105852 A1 | 5/2011 | Morris et al. |
| 2011/0137136 A1 | 6/2011 | Kotanko et al. |
| 2011/0190650 A1 | 8/2011 | McNair |
| 2011/0202486 A1 | 8/2011 | Fung et al. |
| 2011/0208434 A1 | 8/2011 | Hersh |
| 2011/0225006 A1 | 9/2011 | Manning et al. |
| 2011/0238322 A1 | 9/2011 | Song |
| 2011/0276346 A1 | 11/2011 | Reiner |
| 2011/0294673 A1 | 12/2011 | Stacey et al. |
| 2011/0295621 A1 | 12/2011 | Farooq et al. |
| 2011/0295622 A1 | 12/2011 | Farooq et al. |
| 2011/0313788 A1 | 12/2011 | Amland et al. |
| 2012/0215560 A1 | 8/2012 | Ofek et al. |
| 2012/0239420 A1 | 9/2012 | Stapelfeldt et al. |
| 2013/0041683 A1 | 2/2013 | Boissel |

FOREIGN PATENT DOCUMENTS

| | | |
|---|---|---|
| WO | 03/073232 A2 | 9/2003 |
| WO | 03/076895 A2 | 9/2003 |
| WO | 03/104939 A2 | 12/2003 |
| WO | 2006/116622 A2 | 11/2006 |
| WO | 2008/060751 A1 | 5/2008 |
| WO | 2009/038742 A2 | 3/2009 |
| WO | 2010/057184 A2 | 5/2010 |
| WO | 2011/044408 A2 | 4/2011 |
| WO | 2011/071562 A1 | 6/2011 |
| WO | 2011/106709 A2 | 9/2011 |
| WO | 2011/133477 A2 | 10/2011 |
| WO | 2011/149534 A2 | 12/2011 |
| WO | 2011/149608 A1 | 12/2011 |
| WO | 2011/153543 A2 | 12/2011 |

OTHER PUBLICATIONS

Nakamura, Yukari; Notification Concerning Transmittal of Copy of International Preliminary Report on Patentability for PCT Application No. PCT/US2014/030514, dated Sep. 24, 2015; The International Bureau of WIPO; Geneva, Switzerland.

Soliman, Ahmed; Notification of Transmittal of the International Search Report and the Written Opinion of the International Searching Authority for PCT Application No. PCT/US2013/047189; dated Oct. 1, 2013; European Patent Office; Rijswijk, Netherlands.

Moon, Kihwan; Notification Concerning Transmittal of Copy of International Preliminary Report on Patentability for PCT Application No. PCT/US2013/047189; dated Dec. 31, 2014; The International Bureau of WIPO; Geneva, Switzerland.

Wu, J. et al.; "Prediction Modeling using EHR Data: Challenges, Strategies, and a Comparison of Machine Learning Approaches"; Medical Care, vol. 48, No. 6, Suppl. 1; Jun. 2010.

Lehman, Li-wei et al.; "Hypotension as a Risk Factor for Acute Kidney Injury in ICU Patients"; Computing in Cardiology; 2010; ISSN 0276-6574.

Forst & Sullivan; "Strategies and Best Practices in Implementing Healthcare Data Analytics at a Major Urban Medical Center: Denver Health's Experience Using Siemens Decision Support Solutions"; Vital Signs; Oct. 4, 2011.

Blanchette, Joshua B.; Office Action for U.S. Appl. No. 14/578,396; dated Jul. 6, 2017; United States Patent and Trademark Office; Alexandria, Virginia.

Gohari, Mahmood Reza el al.; "Use of an Artificial Neural Network to Determine Prognostic Factors in Colorectal Cancer Patients"; 2011, Asian Pacific J Cancer Prev, 12, 1469-1472.

Microsoft Office Application Help—Excel Help Forum; "Normalizing data formula?"; 2005.

Blanchette, Joshua B.; Final Office Action for U.S. Appl. No. 14/578,396; dated Jan. 12, 2018; United States Patent and Trademark Office; Alexandria, Virginia.

* cited by examiner

PROGRESSION ANALYTICS SYSTEM

CROSS-REFERENCE TO RELATED APPLICATIONS

This application is a continuation of International Application No. PCT/US2014/030514, filed Mar. 17, 2014, entitled "PROGRESSION ANALYTICS SYSTEM", which claims the benefit of U.S. Provisional Patent Application Ser. No. 61/789,695, filed Mar. 15, 2013, entitled "CLINICAL PROGRESSION ANALYTICS SYSTEM", the disclosures of which are incorporated herein by reference.

BACKGROUND

The present disclosure relates in general to development and analytic tools for use in the health care industry that can be utilized for retrospective processing and analysis of medical information.

Many clinical decisions must be made in the typical course of treating a patient who is undergoing medical care. Oftentimes these decisions affect the overall health and well-being of the patient. Particularly, despite current efforts to apply accepted best practices, it is possible for a patient that receives medical care to suffer from an adverse health outcome. Adverse health outcomes originate in many ways which are often occult (latent potential) in the earliest stages of a clinical care process. Examples include iatrogenesis, nosocomial infections, patient safety procedural failures, as well as the natural unchecked progression of a pathologic process or the simple confluence of untoward effects. Further, an adverse outcome may arise in response to, or as a result of, a treatment or procedure designed to treat a diagnosed condition not directly related to the adverse outcome. The occurrence of adverse health outcomes affects the overall burgeoning cost of healthcare.

BRIEF SUMMARY

According to aspects of the present disclosure, a method of identifying insights related to outcomes is provided. The method comprises identifying a patient-care related outcome of interest. The method also comprises extracting electronic clinical data associated with historical healthcare encounters for a plurality of patients, where the plurality of patients include a first subset of patients that experienced the outcome of interest and a second subset of patients that did not experience the outcome of interest. The method further comprises defining patient groups based upon similar data patterns present in the extracted electronic clinical data, where the data patterns are selected such that the defined patient groups differentiate from one another in terms of a likelihood of the outcome of interest, consequences associated with the outcome of interest or both. The method still further comprises deriving hypothesized etiological explanations for why one or more patient groups have a different likelihood, consequence or both, with respect to the outcome of interest when compared to other patient groups.

Optionally, the method comprises identifying clinical interventions that are intended to modify the likelihood and/or consequences of the outcome of interest for certain patient groups. The method may be applied with the objective of decreasing the likelihood and/or consequences of an adverse outcome or to increase the likelihood and/or consequences of a favorable outcome.

DETAILED DESCRIPTION

Figure 1:
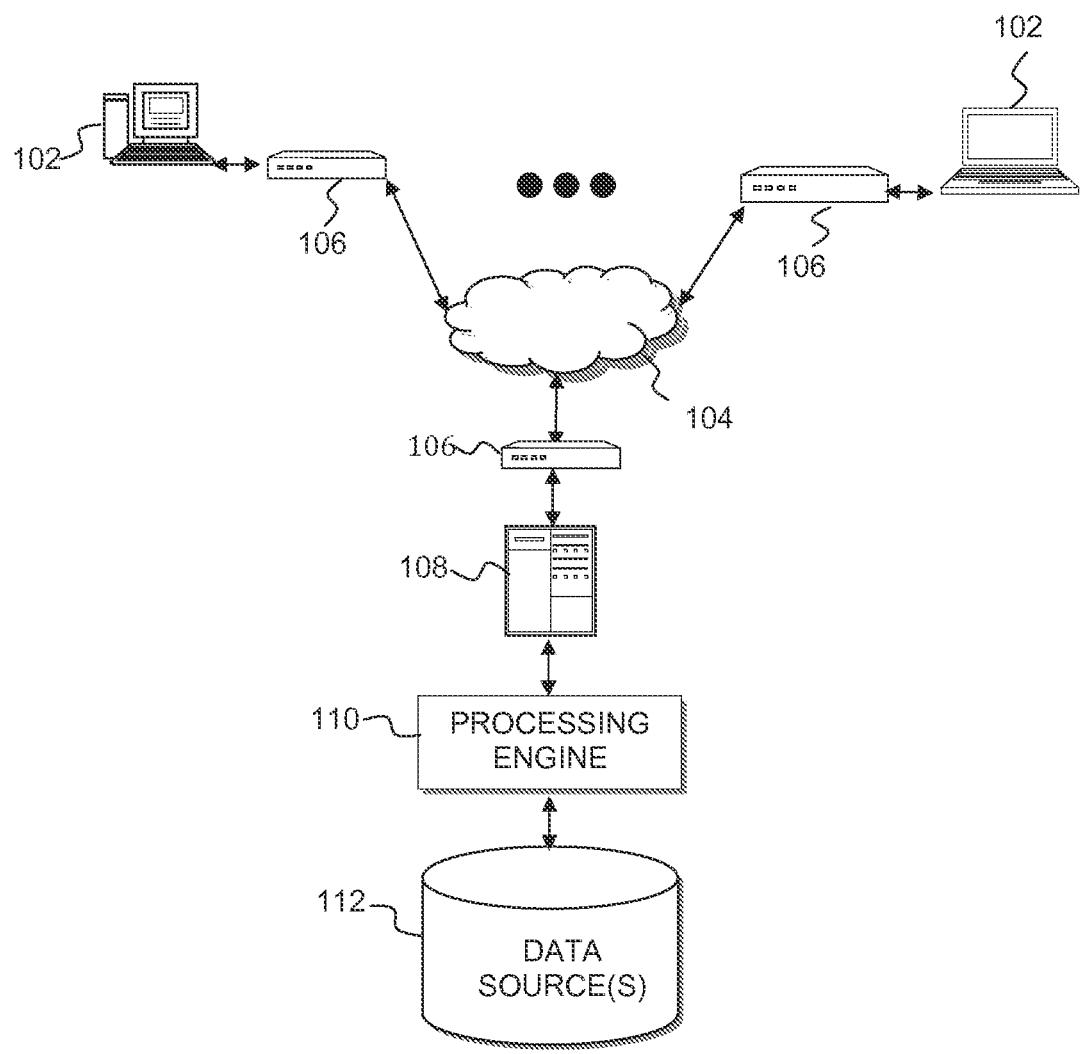
FIG. 1 is a block diagram of a basic computer system that may be used to implement a progression analytics system, according to aspects of the present disclosure.

According to various aspects of the present disclosure, a progression analytics system is provided, which is utilized to extract electronic clinical data associated with historical healthcare encounters based upon a patient-care related outcome of interest. The progression analytics system is further utilized to define patient groups based upon similar data patterns present in the extracted electronic clinical data. The patient groups are defined such that the patient groups may have a varying likelihood that the outcome of interest will occur, varying consequences associated with the outcome of interest, or both. Based upon an analysis of the patient groups, hypothesized etiological explanations are derived for explaining the differences among the patient groups with regard to the outcome of interest. For instance, the etiological explanations may attempt to explain why one or more patient groups have a different likelihood for the outcome of interest, why one or more patient groups have a different consequence associated with the outcome of interest, or both, when compared to other patient groups. These etiological explanations can be utilized to define interventions and other treatment changes that may be included in patient care protocols to improve patient care.

Clinical Progression:

The care seeking behavior of individuals most commonly begins when they experience signs and/or symptoms of an illness or experience some form or trauma. The clinical encounter begins when the individual is presented to healthcare personnel. At the outset of the clinical encounter, the individual is identified as a "patient" and a healthcare record is initiated. The individual's symptoms, which are usually subjective complaints, are recorded in the healthcare record. Signs observed by the clinician are also recorded in the healthcare record. Both signs and symptoms may be indicative that a pathologic (disease) process is in progress. Conversely, both signs and symptoms may represent normal physiologic processes and not be indicative of a pathologic process.

Typically, the clinician(s) initiate a diagnostic process based upon the patient's signs and symptoms. This diagnostic process often includes a patient evaluation, the nature of which depends upon the acuity (severity) of the illness/injury and the clinician's determination whether the initial signs and symptoms represent a potentially urgent or emergent patient need. From this early collection of information and a physical examination, laboratory and other testing is typically ordered by the clinician in an effort to establish or rule/out various diagnoses.

A plan of action is implemented as indicated by the patient's clinical condition and in light of any early results available from the tests ordered. At this point, the object of care is to establish and maintain normal homeostatic physiologic functions. However, patient care is also carried out to correct any physiologic functions found to be abnormal, to identify pathologic processes causing or contributing to the abnormal physiologic functions, to provide definitive care aimed at eliminating the culprit pathologic process restoring the individual to prior level of health, etc.

All of the above information may be electronically captured during a healthcare encounter associated with the patient, and represents examples of 'clinical data'. Moreover, the patient's experience going through these various stages or steps is referred to herein as a 'clinical progression'. The continuation of underlying disease process is called the 'pathologic progression'. The goal of treatment is to stop the pathologic progression and restore normal homeostatic function at least to the previous level of health prior to the illness/injury.

In the course of care, it is possible for a patient to experience a favorable outcome. It is also possible for a patient to experience an adverse outcome. Potential adverse outcomes may be subdivided into "active" and "latent." 'Active adverse outcomes' can be characterized as known potentially negative consequences or results that may occur due to an intended clinical intervention. Medications, surgical procedures, patient safety, infections, and childbirth provide well-known examples. 'Latent potential adverse outcomes' are much less well understood. A latent adverse outcome may occur unexpectedly even when the clinical care process is going well. For instance, latent adverse outcomes may result from an unexpected reaction to treatment, or a confluence of untoward effects. Latent adverse outcomes may also be attributed to "chance" because the nature of the occurrence is not known or understood.

According to various aspects of the present disclosure, systems, methods and computer program products implement development and analysis tools useful for the retrospective processing of medical information, in a manner that facilitates the systematic analysis of the likelihood and/or consequences of an outcome of interest based upon electronic clinical data. The outcome may be adverse or favorable. The analysis may be directed to the likelihood of an occurrence of an outcome of interest. Alternatively, the analysis may be directed to the consequences associated with an outcome of interest (e.g., degree, severity, duration, etc.). Moreover, the above variations in analysis may be performed in combination, e.g., by analyzing a combination of likelihood and consequences, etc.

Platform Overview:

Referring now to the drawings and particularly to FIG. 1, a general diagram of a computer system 100 is illustrated, where components of the computer system 100 can be used to implement elements of a progression analytics system according to aspects of the present disclosure. In this regard, the computer system 100 may be utilized to implement the methods and processes described with reference to FIGS. 2-7 herein.

The computer system 100 can be deployed in a wide variety of manners, including within an outpatient office/clinic, hospital, integrated healthcare network (IHN), within a location outside of where direct patient care is provided, etc. In this regard, the computer system 100 or components thereof can be distributed across multiple different locations including multiple IHNs simultaneously. Moreover, computer system components can be implemented by different entities with or without sharing data between the entities. Regardless of deployment strategy, the computer system 100 can be implemented by a source tasked with identifying insights related to the occurrence of an outcome of interest, such as an adverse health outcome.

The computer system 100 comprises a plurality of processing devices, designated generally by the reference 102 that are linked together by a network 104. As will be described more fully herein, some processing devices 102 of the computer system 100 are used for model and algorithm development, creation, maintenance, etc., whereas some processing devices 102 are used in a corresponding clinical application, e.g., as a user interface utilized by treating clinicians or analysts to execute or otherwise implement the methods, processes and computer program products described herein.

As a few illustrative examples, the processing devices 102 can include servers, personal computers and portable computers. As used herein, portable computers include a broad range of processing devices, including notebook computers, tablet computers, transactional systems, purpose-driven appliances (e.g., networkable medical machines), special purpose computing devices, personal data assistant (PDA) processors, cellular devices including smart telephones and/or other devices capable of communicating over the network 104.

The network 104 provides communications links between the various processing devices 102, and may be supported by networking components 106 that interconnect the processing devices 102, including for example, routers, hubs, firewalls, network interfaces, wired or wireless communications links and corresponding interconnections, cellular stations and corresponding cellular conversion technologies, e.g., to convert between cellular and tcp/ip, etc. Moreover, the network 104 may comprise connections using one or more intranets, extranets, local area networks (LAN), wide area networks (WAN), wireless networks (WIFI), the Internet, including the World Wide Web, and/or other arrangements for enabling communication between the processing devices 102.

The illustrative progression analytics system 100 also includes a server 108, which executes at least one processing engine 110 that interacts with at least one corresponding data source 112. The processing engine(s) 110 and data source(s) 112 may be used to support the progression analytics system, e.g., by executing one or more aspects of the methods described with reference to FIGS. 2-7, as described in greater detail herein. The results of the processing performed by the server 108 can be communicated to the processing devices 102, e.g., which may be stationed in hospital offices, at centralized locations, at remote locations, etc.

The flows, methods, processes, etc., described with reference any of FIG. 2-FIG. 7 herein can be implemented on one or more of the system components of FIG. 1, e.g., the processing engine 110 executing on the server 108. Moreover, the flows, methods, processes, etc., with reference to any of FIG. 2-FIG. 7 can be implemented as methods or computer program product code that is embodied on a computer readable storage media. In this configuration, the code is executable by a processor to cause the processor to perform the corresponding methods set out herein.

Figure 2:
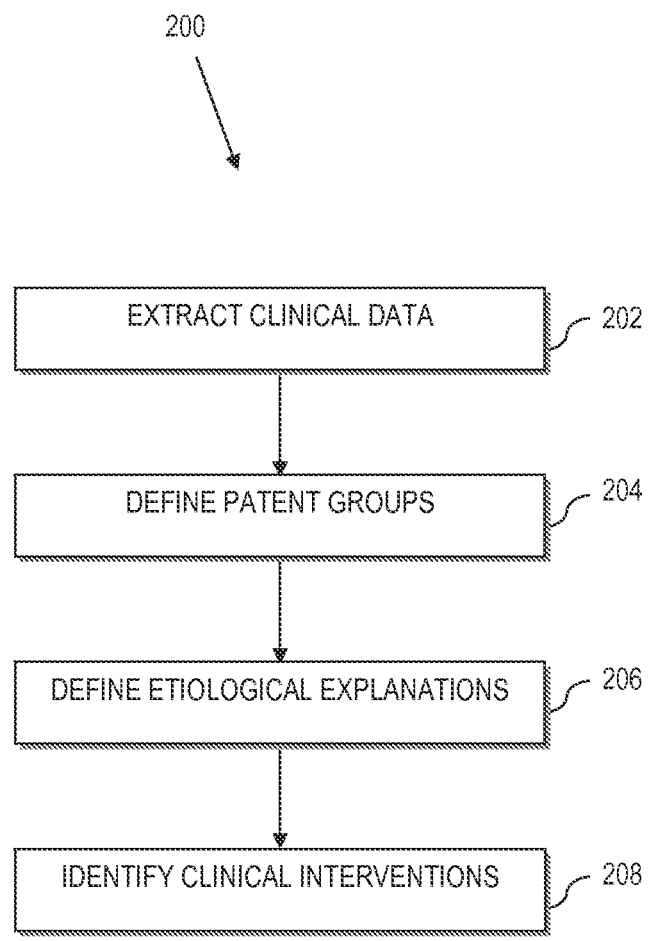
FIG. 2 is a flow chart of an exemplary flow within a progression analytics system that provides development and analysis tools useful for retrospective processing of medical information with respect to outcome of interest, according to aspects of the present invention.

Progression Analytics:

Referring to FIG. 2, a computer-implemented method 200 is provided for identifying insights related to the occurrence of a patient care-related outcome of interest, e.g., an adverse health outcome. The method 200 includes extracting, at 202, electronic clinical data associated with historical healthcare encounters for a plurality of patients. Here, the plurality of patients associated with the extracted electronic clinical data includes a first subset of patients that experienced the outcome of interest, and a second subset of patients that did not experience the outcome of interest. An example method of extracting the electronic clinical data is described with regard to FIG. 3.

As used herein, 'electronic clinical data' is electronically stored data that relates to healthcare encounters of individuals. Electronic clinical data may include electronic patient information such as demographic data, patient medical historical data, physician practice information, ambulance/emergency care information, laboratory results, triage results, measured vitals, electronic health records, etc.

Electronic clinical data may also include information that is utilized by a progression analytics system implementing the method of FIG. 2. For instance, the electronic clinical data can include 'likelihood variables', 'consequence variables', an 'outcome likelihood model', outcome likelihoods that are computed for patients having a healthcare encounter included within the electronic clinical data, a 'consequence likelihood model', outcome consequences that are computed for patients having a healthcare encounter included within the electronic clinical data, attributions of outcome likelihood to causal factors, combinations thereof, etc.

As used herein, 'likelihood variables' are variables characterized as expressions, functions or other extractions based upon electronic patient information, which have a reconcilable relationship with an etiology of a corresponding outcome of interest, or which may be generated based upon a computed statistical relationship for predicting an associated outcome of interest. In this regard, likelihood variables may be extracted directly from electronic patient information or likelihood variables may be derived from electronic patient information. Moreover, the likelihood variables can be derived from datasets that are the same as, or different from the electronic patient information included in the electronic clinical data. In illustrative implementations, likelihood variables relate to the probability of occurrence of an outcome of interest.

As used herein, 'likelihood factors' are concepts that characterize factors that are of interest in predicting the likelihood of a particular outcome of interest (and for which a model is to be trained). In general, likelihood factors may be based upon outcome specific etiological knowledge such as causal relationships, conditions, origins, or reasons for an outcome specific condition.

As used herein, an 'outcome likelihood model' is a model that estimates the likelihood of the outcome of interest using a group of likelihood variables. In certain implementations, the outcome likelihood model may be implemented as a 'baseline and dynamic outcome likelihood model'. In this instance, each likelihood variable is classified into either a baseline group or a dynamic group. Here, the baseline group is composed of variables that hold a non-modifiable expression (e.g., constant value for a given patient healthcare encounter, such as date of admittance). Correspondingly, the dynamic group is composed of variables that can store a modifiable expression (e.g., an expression having a value that can change over a given patient healthcare encounter, such as heart rate).

As used herein, an 'outcome likelihood' is a likelihood that a particular outcome of interest will occur, which is determined using an outcome likelihood model.

As used herein, 'consequence variables' are variables characterized as expressions, functions or other extractions based upon electronic patient information, which have a reconcilable relationship with an etiology of a corresponding outcome of interest, or which may be generated based upon a computed statistical relationship for predicting the consequences associated with an outcome of interest. In this regard, consequence variables are similar to likelihood variables, and may be extracted directly from electronic patient information or consequence variables may be derived from electronic patient information. Moreover, the consequence variables can be derived from datasets that are the same as, or different from the electronic patient information included in the electronic clinical data. In an illustrative implementation, consequence variables do not specifically relate to the probability of an occurrence of on outcome of interest. Rather, consequence variables relate to other factors that follow or otherwise relate to consequences of the outcome of interest, such as may be measured in time, duration, degree, severity, etc. Thus, an outcome of interest may occur across two or more patients. However, that outcome may vary in numerous different measures of impact, which may all be characterized by consequence.

As used herein, 'consequence factors' are concepts that characterize factors that are of interest in predicting the consequences associated with a particular outcome of interest (and for which a model is to be trained). In general, consequence factors may be based upon outcome specific etiological knowledge such as causal relationships, conditions, origins, or reasons for an outcome specific condition.

As used herein, an 'outcome consequence model' is a model that estimates consequences of the outcome of interest using a group of consequence variables. In certain implementations, the outcome consequence model may be implemented as a 'baseline and dynamic outcome consequence model' in a manner analogous to the baseline and dynamic likelihood model.

As used herein, an 'outcome consequence' is a consequence associated with a particular outcome of interest, which is determined using an outcome consequence model.

As used herein, 'attribution' is information related to providing insight as to those likelihood variables that are likely leading to the computed assessment of likelihood of the outcome of interest.

Further examples of defining the likelihood and consequence variables, an outcome likelihood model and attributions are set out in PCT Pat. App. No. PCT/US13/47189, to Haber et al., entitled "Clinical Predictive Analytics System" filed Jun. 21, 2013, the disclosure of which is herein incorporated by reference in its entirety.

A feature of the method 200 that provides an inventive technical contribution includes defining, at 204, patient groups among the plurality of patients, where each patient group is defined by grouping together those patients having a similar data pattern present in their corresponding extracted electronic clinical data.

Examples of data patterns are provided throughout. However, as a few examples, a patient group may be defined as including at least one patient from the first subset of patients and at least one patient from the second subset of patients. In this manner, at least one patient group will include patient(s) that did experience the outcome of interest, and patent(s) that did not experience the outcome of interest. Moreover, the specific use of trajectories to define data patterns is described with reference to FIG. 7.

For example, the method 200 may divide the plurality of patients up into patient groups such that each patient belongs to only one patient group. Moreover, in an illustrative implementation, the data patterns are selected or otherwise generated such that the defined patient groups differentiate from one another based upon the likelihood and/or consequences of the outcome of interest. As a few illustrative examples, the data patterns may be defined to differentiate the groups based upon a likelihood of an occurrence of the outcome of interest (including cases where a group may have a likelihood of 0). As another example, the data patterns may be utilized to differentiate the groups based upon a varying consequence in an outcome of interest. As an illustration, an adverse outcome may be unavoidable. However, groups may have experienced a different consequence of the outcome of interest, e.g., in terms of degree, severity, duration, etc. An illustrative method of defining patient groups is described with regard to FIG. 4. Moreover, an example method of deriving the data patterns from the extracted electronic clinical data, and grouping together those patients having a similar data pattern, is described with reference to FIG. 4.

Yet another feature of the method 200 that provides an inventive technical contribution includes deriving, at 206, hypothesized etiological explanations for why one or more patient groups have variations in the likelihood and/or consequences of the outcome of interest when compared to other patient groups. As noted in greater detail herein, the explanations may attempt to explain likelihood of occurrence, consequence, combinations thereof (such as risk), etc. An example method of defining hypothesized etiological explanations is described with regard to FIG. 5.

The method 200 can be implemented in a manner such that the patient care-related outcome of interest is selected as a favorable health outcome. In this regard, hypothesized etiological explanations may attempt to explain why one or more patient groups experienced an increase in the likelihood and/or favorable consequences of the favorable health outcome relative to other patient groups.

As another example, the method 200 can alternatively be implemented in a manner such that the patient care-related outcome of interest is selected as an adverse health outcome. In this regard, hypothesized etiological explanations may attempt to explain why one or more patient groups have a different risk (e.g., likelihood of occurrence, consequence, or a combination thereof) associated with the outcome of interest, relative to other patient groups. The etiological explanations may attempt to explain the reasons that decrease the risk, e.g., likelihood and/or negative consequences, of a select patient group attaining the adverse health outcome, regardless of whether a particular adverse outcome instance was active or latent.

As an optional process, the method 200 may also include identifying, at 208, clinical interventions that have the potential to impact the likelihood and/or consequences of an outcome of interest, e.g., to lower the likelihood of the adverse health outcome. An example method of identifying clinical interventions is described with regard to FIG. 6.

Figure 3:
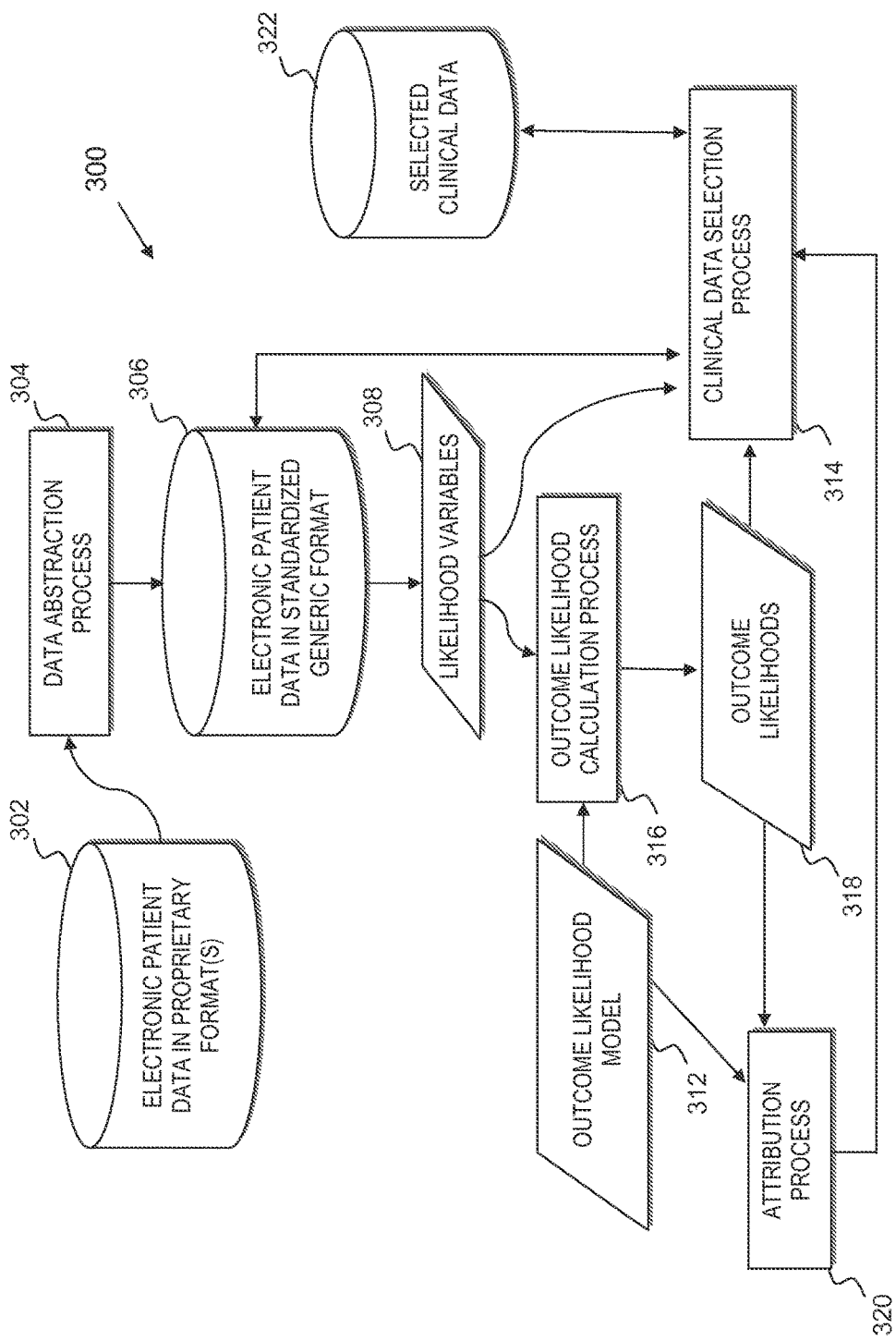
FIG. 3 is a flow diagram illustrating the use of models and algorithms in a progression analytic system to generate relevant electronic clinical data for use with the flow of FIG. 2, according to aspects of the present disclosure.

Clinical Data Extraction:

Referring to FIG. 3, a computer-implemented component 300 of a progression analytics system is provided for identifying electronic clinical data, e.g., for extracting at 202 of FIG. 2, for defining patient groups at 204 of FIG. 2 etc.

In the exemplary component 300, electronic patient data is provided in a data source 302. As noted in greater detail herein, the electronic patient data can include information collected as a result of patient healthcare encounters, such as demographic data, patient medical historical data, physician practice information, ambulance/emergency care information, laboratory results, triage results, measured real time vitals, electronic health records, patient medical history, etc.

The electronic patient data may be electronically stored in the data source 302 as structured or unstructured data, in a proprietary format or otherwise. Also, the electronic patient data may include historical patient data to be analyzed, including patient data for healthcare encounters related to an outcome of interest, patient data for healthcare encounters not related to an outcome of interest or combinations thereof. As such, it may be necessary to prune the available data in the data source 302 to generate electronic clinical data that is determined to be statistically relevant to the analysis of the outcome of interest.

An optional data abstraction process 304 receives as input, the electronic patient data from the data source 302, which may be in proprietary format(s) and converts, transforms, etc., (i.e., maps) the proprietary data to a standardized generic format, schematically represented by the data source 306. Moreover, the conversion of patient data to a standardized format is optional and may not be necessary, e.g., where the patient data is already available in a data format suitable for processing.

Likelihood Variables:

Likelihood variables 308 that are determined to be relevant to the likelihood of the outcome of interest, are extracted from, computed from, or otherwise derived from (i.e., mapped from) the electronic patient data 306 (if the likelihood variables 308 are not otherwise available from another source, e.g., pre-computed). As noted above, the likelihood variables may be generated so as to have a reconcilable relationship with an etiology of the outcome of interest. As another example, likelihood variables may be generated based upon a computed statistical relationship for predicting the occurrence of the outcome of interest.

In an illustrative example, a system user such as a healthcare data analyst or a clinical subject matter expert interacts with the component 300 of the progression analytic system through a graphical user interface (GUI) to perform a likelihood variable selection process. Briefly, in an exemplary approach, outcome specific etiological knowledge is transformed into likelihood factors, and those likelihood factors are reconciled into likelihood variables.

In this example, the system user utilizes outcome specific etiological knowledge to identify likelihood factors, e.g., concepts that characterize factors that are of interest in predicting the likelihood of the particular outcome of interest (and for which a model is to be trained). In general, the outcome specific etiological knowledge may include causal relationships among likelihood factors, conditions, origins, or reasons for an outcome specific condition.

The system user interacts with the component 300 of the progression analytics system through the GUI to construct likelihood variables 308 that reconcile with the identified likelihood factors. Here, the likelihood variables 308 may be calculated, derived, transformed, mapped or otherwise obtained from the electronic patient data in the data source 306.

Likelihood variables may also be generated using the methods and techniques set out in PCT Pat. App. No. PCT/US13/47189, to Haber et al., entitled "Clinical Predictive Analytics System" filed Jun. 21, 2013, the disclosure of which is already incorporated by reference in its entirety.

Outcome Likelihoods:

The system user may further interact with component 300 of the progression analytics system through the GUI to construct an outcome likelihood model 312.

As an illustrative example, an outcome likelihood model form and variable selection process is guided by a training data set (e.g., a subset of data within the electronic patient data 306) that includes both outcome data and non-outcome data. In an illustrative example, the outcome likelihood model form and variable selection process outputs a model that takes the general form: $Y=\log(P/(1-P))=\beta_0+\beta_1 x_1+ \ldots +\beta_k x_k$. In this example implementation, estimated outcome likelihoods are computed based upon logistic regression models, thus predicting the likelihood that a person will experience an outcome of interest in the near future, e.g., during the healthcare encounter. In this example, there are k likelihood variables where $\beta_1$-$\beta_k$ represent model coefficients. In practice, the training data set is used to fit the model. The model then determines if $\beta$ should be adjusted up or down, whether factor $x_i$ should be dropped, etc. The model itself determines which parameters are important.

In an exemplary configuration, the likelihood variables 308 are divided into baseline likelihood variables and dynamic likelihood variables. Variables deemed to be non-modifiable based on the medical care that is provided to the patient are classified as baseline likelihood variables (also referred to generally as baseline variables). Correspondingly, variables affected by the medical care that the patient receives while in the hospital will be classified as dynamic likelihood variables (also referred to generally as dynamic variables). The baseline and dynamic likelihood variables and the training set are utilized to generate baseline and dynamic likelihood model forms at 312.

Baseline and dynamic outcome likelihood models may also be generated for use at 312 using the methods and techniques set out in PCT Pat. App. No. PCT/US13/47189, to Haber et al., entitled "Clinical Predictive Analytics System" filed Jun. 21, 2013, the disclosure of which is already incorporated by reference in its entirety.

Clinical Data Selection:

As noted in greater detail herein, the progression analytic system extracts clinical data associated with historical healthcare encounters for patients that are selected for the evaluation of an outcome of interest. In this regard, a clinical data selection process 314 is utilized to select the clinical data that will be utilized for the analysis. In an illustrative example, a system user interacts with the component 300 of the progression analytics system through a GUI to establish inclusion criteria to filter the data in the data source 306 to selectively extract patients having relevant historical healthcare encounter data (which include patients that experienced the outcome of interest and patients that did not experience the outcome of interest).

As an illustrative example, the clinical data selection process 314 interacts with the data source 306 to input patient healthcare encounters into an outcome likelihood calculation process 316, which uses the likelihood variables 308 and the outcome likelihood model(s) 312 to compute outcome likelihoods 318 for the selected healthcare encounters. The clinical data selection process 314 applies inclusion and/or exclusion criteria to filter the healthcare encounter data such that only selected patient data is organized as the set of clinical data stored at 322.

To ensure the selection of meaningful patient healthcare encounters, the clinical data selection process 314 may utilize the inclusion/exclusion criteria to place restrictions on the likelihood variable values for a patient healthcare encounter under consideration. As further examples, the inclusion/exclusion criteria may be evaluated against the results of the outcome likelihood computations at 318. As yet a further example, the inclusion/exclusion criteria can take other factors into consideration, such as demographics, etc.

In certain illustrative implementations, the clinical data selection process 314 may further utilize an attribution process 320 to provide information as to which likelihood variables are driving the computed outcome likelihoods 318. For example, the attribution process 320 may characterize the degree to which likelihood for the outcome of interest can be attributed to individual likelihood variables or collections of likelihood variables. This information can be processed through the inclusion/exclusion criteria to determine if the patient healthcare encounter should be selected into the clinical data 322.

As noted in greater detail herein, the selected clinical data stored at 322 can also include the likelihood variables 308, the computed outcome likelihoods 318 and other data. Moreover, in certain illustrative implementations, the selected electronic clinical data can include trajectory data. Trajectory data is electronic clinical data that includes information that is analyzed for generating care element trajectories as will be described in greater detail, with reference to FIG. 7.

The selected electronic clinical data 322 may be utilized as the electronic clinical data extracted at 202 of FIG. 2. However, other techniques and approaches may alternatively be implemented to select the electronic clinical data utilized by the method 200 of FIG. 2.

In alternative configurations, it may be more desirable to measure consequence rather than likelihood. Here, the component 300 of a progression analytics system may be provided, where the likelihood variables, likelihood factors, outcome likelihood, etc. are replaced with consequence variables, consequence factors, outcome consequences, etc.

Figure 4:
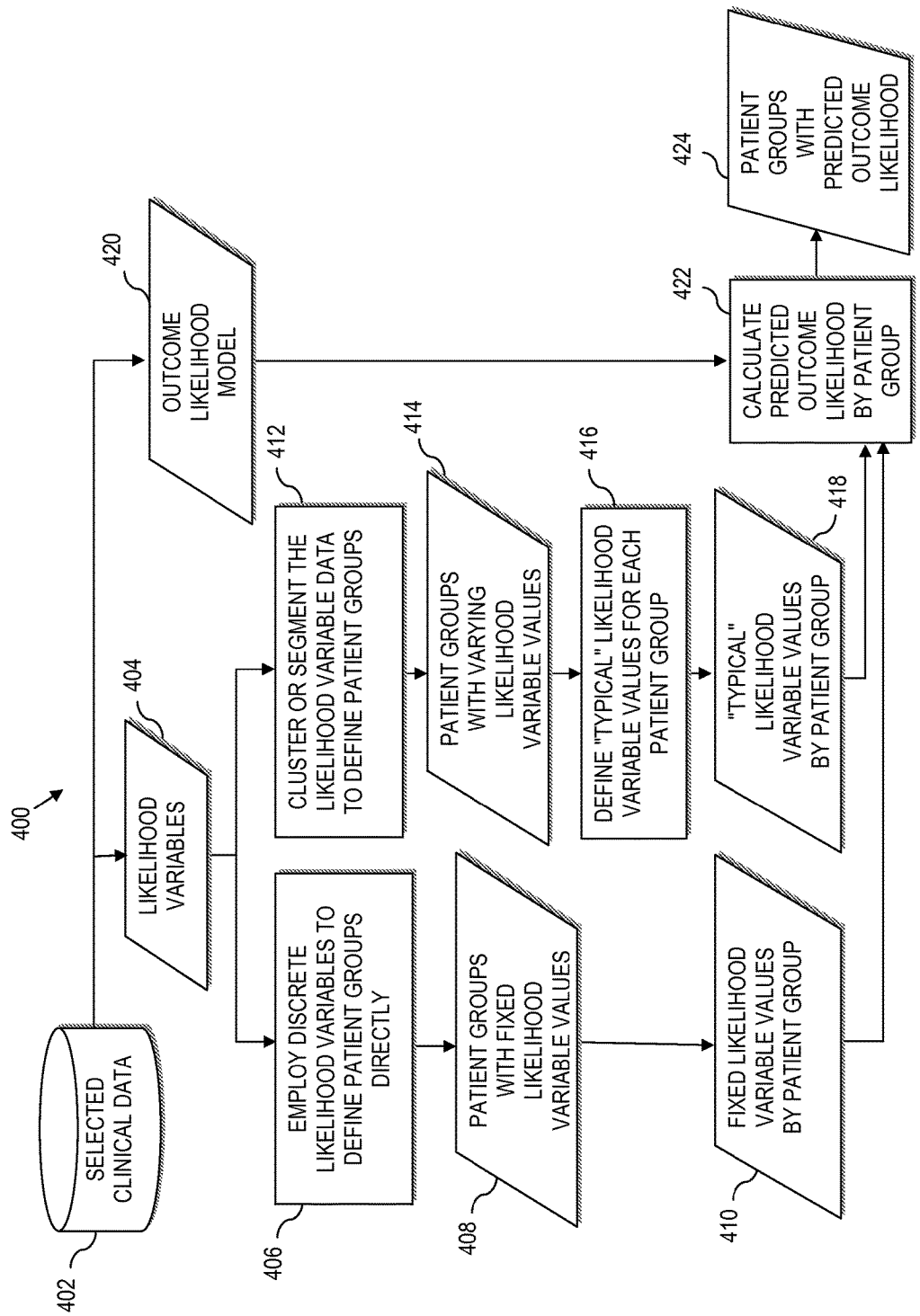
FIG. 4 is a flow diagram illustrating an approach to define patient groups, for use with the flow of FIG. 2, according to aspects of the present disclosure.

Group Identification:

Referring to FIG. 4, a computer-implemented component 400 of a progression analytics system is provided to define patient groups, e.g., at 204 of FIG. 2.

The component 400 utilizes selected electronic clinical data in data source 402. In an exemplary implementation, the information in the data source 402 is the electronic clinical data stored in the data source 322 (i.e., selected electronic clinical data) described with reference to FIG. 3. Alternatively, the data source 402 may comprise selected electronic clinical data that was selected using alternative approaches.

As noted in greater detail herein, patient groups are defined by grouping together those patients having 'similar data patterns'. However, a patient may generate a significantly large amount of data during a healthcare encounter. As such, to maintain manageable populations of groups, the data pattern describing each group can be based upon a finite number of measures. Moreover, a "pattern" defining a group can be based upon measures that are defined in terms of a specific data value, ranges of values, transitions over time, or any other desired manner to designate the requirements for membership to a particular group. Still further, data patterns may be determined based upon trajectory, as described in greater detail with reference to FIG. 7.

It is likely that not all of the patient data will contribute significantly to the outcome of interest. As such, the component 400 can use likelihood variables 404 for consideration of the selection of the groups. The likelihood variables at 404 may be the likelihood variables 308 described with reference to FIG. 3, or a subset thereof. Alternatively, the likelihood variables at 404 can be derived from the patient data, e.g., using techniques as set out more fully herein, or using other techniques.

The component 400 employs a process at 406 that contributes to defining one or more patient groups (e.g., as set out in 204 of FIG. 2). In this regard, the process at 406 processes one or more discrete likelihood variables. Here, 'discrete' likelihood variables refers to a subset of the likelihood variables 404 for which a likelihood variable takes on one of a finite set of discrete values, or where a measure can be defined that expresses a discrete representation of a corresponding likelihood variable 404 (or group of likelihood variables 404). In this regard, the component 400 generates at 408, patient group(s) with fixed likelihood variable values. The component 400 may also generate at 410, fixed likelihood variable values by patient group.

By way of example, a likelihood variable may have one of a limited number of values, e.g., a binary value. In other instances, a likelihood variable value is compared to a threshold or range of thresholds to transform the value of the likelihood variable into a discrete value. In illustrative examples, a system user can interact with the progression analytics system through a GUI to set the thresholds, adjust the thresholds or otherwise manipulate the process 406 processing parameters.

By way of example, the system user may utilize the GUI of the component 400 to select a subset of likelihood variables 404, then transform the values for patient healthcare encounters corresponding to that subset of likelihood variables 404 into discrete values (e.g., binary, or other number of discrete values) based upon thresholds, rules, algorithms, etc.

In many cases, the process 406 is sufficient to generate the patient groups necessary for further evaluation. However, in certain cases, there are likelihood variables of interest that have analog values, values that change over time, or are otherwise difficult to transform into discrete representations (measures). As such, the component 400 also (or alternatively to the process 406) implements a process 412 that also contributes to defining patient groups (e.g., as set out in 204 of FIG. 2). For instance, the process 412 may cluster or otherwise segment the extracted electronic clinical data and define a patient group for each data cluster or segment. For example, the process 412 may accept a patient into a particular group based upon a computation that places the clinical data associated with the healthcare encounter for that patient within a user-defined range of a centroid in a cluster.

In the context of FIG. 4, the process at 412 clusters or segments the patient healthcare encounter data to define patient groups. The output of the process at 412 is a defined set of patient groups 414, wherein the patient groups may have varying values for one or more of the likelihood variables. The patient groups and corresponding likelihood variable data at 414 are provided to a process at 416 that defines "typical" likelihood variable values for each patient group. The output of the process at 416 is data at 418 that defines "typical" likelihood variable values by patient group.

In illustrative examples, the system user can interact with the component 400 of the progression analytics system through a GUI to set the clustering algorithms, adjust the thresholds, centroid range, or otherwise manipulate the process 412 processing parameters.

In yet further implementations, the patient groups may be defined based upon a combination of discrete likelihood variable representations and clustered (e.g., analog) likelihood variables. As such, the set of possible groups may be defined solely by the process 406, solely by the process 412, or by a combination of the process 406 and process 412, depending upon the nature of the likelihood variables 404. Further, the data patterns employed to define patient groups may include defining values of one or more static variables that do not change during the course of a hospital encounter and/or defining a pattern across a time history of changes in the physiological state of patients, occurrences of events that the patients experience, or both.

The component 400 also includes an outcome likelihood model at 420, which receives as input, data from the data source 402. The outcome likelihood model at 420 may be the outcome likelihood model 312 described with reference to FIG. 3, or a model that is constructed using other techniques. For instance, the outcome likelihood model 420 may be developed as an outcome likelihood scoring algorithm that characterizes the likelihood of a specific outcome as a function of variables derived from the data stored in the data source 402, e.g., the extracted clinical data. This facilitates a process at 422 having the ability to define patient groups based on data patterns in the variables employed in a scoring algorithm. In yet another alternative configuration, the outcome likelihood model may be implemented as the calculation of actual likelihood for historical patients belonging to the patient groups.

The component 400 also includes a process 422 that calculates a predicted outcome likelihood by patient group, using as inputs, the fixed likelihood variable values by patient group at 410, and/or the "typical" likelihood variable values by patient group at 418, and the outcome likelihood model at 420. The output of the process at 422 is data at 424 that represents patient groups with predicted outcome likelihood. As such, the process of FIG. 4 defines patient groups among the plurality of patients, where each patient group is defined by grouping together those patients having a similar data pattern present in the extracted electronic clinical data, where the defined patient groups have varying likelihood for the adverse health outcome of interest.

In further exemplary implementations, the process 422 may compute or otherwise receive as input, a calculation representing the actual percentage of patient healthcare encounters in each group that experienced the outcome of interest. As such, the process 422 can compare the actual percentage of patient healthcare encounters in each group that experienced the outcome of interest with the corresponding computed likelihood of an occurrence of the outcome of interest. This comparison can be utilized to provide confidence in the selection of the relevant parameters. For instance, a strong correlation between the computed likelihoods and actual percentages provides confidence that the analysis will provide meaningful results. If the computed likelihoods and actual percentages do not correlate, then there could be an issue with the selection of likelihood variables 404, with the model form of the outcome likelihood model 420, with the thresholds or other parameters utilized by the system user to process the patient healthcare encounters, etc. This provides an opportunity for feedback to make adjustments to the previous processes and methods.

As noted in greater detail, a patient group may be defined as including at least one patient from the first subset of patients and at least one patient from the second subset of patients. In this manner, at least one patient group will include patient(s) that did experience the outcome of interest, and patent(s) that did not experience the outcome of interest.

Moreover, as noted above, patients having a similar data pattern present in their corresponding extracted electronic clinical data may be grouped by defining similar data patterns based upon the data values of a subset of the likelihood variables, consequence variables or both, such that the patient groups are defined in terms of variables and not in terms of whether or not the patient has experienced the outcome of interest. Moreover, the subset of the likelihood variables, consequence variables or both, may be converted into discrete measures having a fixed number of value options. Thus, methods herein may group together those patients having the same data values associated with the discrete measures.

According to various aspects of the present disclosure, the organization of the patient groups results in groups having different likelihoods of the outcome of interest. In alternative configurations, it may be more desirable to measure consequence rather than likelihood. Here, the component 400 of a progression analytics system may be provided, where the likelihood variables, discrete likelihood variables, outcome likelihood model, predicted outcome likelihood, etc., are replaced with consequence variables, discrete consequence variables, outcome consequence model, predicted outcome consequence, etc.

Hypothesized Etiological Explanations:

According to aspects of the present invention, the progression analytics system provides a GUI that enables a system user to derive hypothesized etiological explanations that correlate with comparisons of various patient groups.

Figure 5:
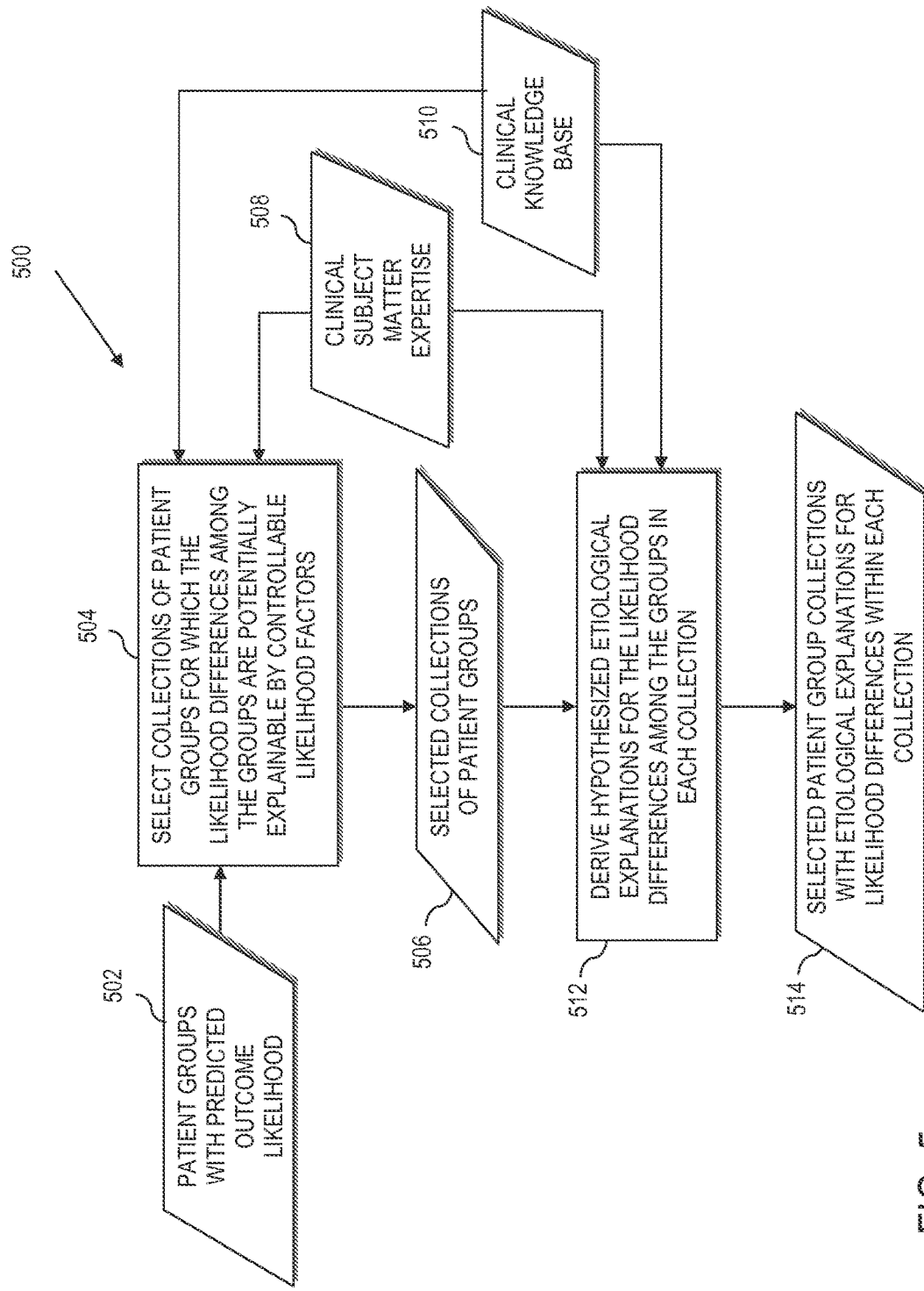
FIG. 5 is a flow diagram illustrating an approach for defining etiological explanations that explain differences among patient groups, according to aspects of the present disclosure.

Referring to FIG. 5, a component 500 is provided for selecting one or more collections of patient groups to derive hypothesized etiological explanations for the likelihood differences among the patient groups in each collection. For example, explaining why one patient group in a collection has a higher likelihood of the outcome of interest than another patient group in the collection. For example, in an exemplary implementation, the component 500 or other interface associated with the progression analytics system presents to the system user a series of patient group pairs. For each pair, the system reports the difference in outcome likelihood between the two groups in each pair and reports the likelihood variables that are most different for the two groups in each pair, e.g., the distinguishing likelihood variables. The system user may then interact with the reported information to first select patient group pairs with large likelihood differences and then select patient group pairs for which the distinguishing likelihood variables derive from likelihood factors that have the potential to be controllable via patient care protocols.

The component 500 starts with data at 502 that defines patient groups with predicted outcome likelihood. For instance, the data at 502 may comprise the data at 424 that is generated by the component 400 described with reference to FIG. 4. A process at 504 selects collections of patient groups for which the likelihood differences among the groups are potentially explainable by controllable likelihood factors.

This selection process may be implemented by a system user interacting with the progression analytics system though a GUI. The process at 504, which can select collections of patient groups for which the likelihood differences among the groups are potentially explainable by the controllable likelihood factors, outputs data at 506 that defines selected collections of patient groups. As illustrated, the process at 504 may include inputs from other sources, including data at 508 corresponding to clinical subject matter expertise, data at 510 corresponding to data extracted from a clinical knowledgebase, combinations thereof, etc. A process at 512 receives as input, the data at 506 representing the selected collections of patient groups. The process at 512 may also include inputs from other sources, including data at 508 corresponding to clinical subject matter expertise, data at 510 corresponding to data extracted from a clinical knowledgebase, combinations thereof, etc.

The clinical knowledgebase 510 is an information repository that provides a means for clinical information to be collected, organized, shared, searched and utilized. In this manner, the clinical knowledgebase 510 represents a knowledge repository that is organized by physiological condition or adverse outcome and captures knowledge about operating in the clinical setting. An example of approaches for constructing the clinical knowledgebase 510 is described more fully in PCT Pat. App. No. PCT/US13/47189, to Haber et al., entitled "Clinical Predictive Analytics System" filed Jun. 21, 2013, the disclosure of which is already incorporated by reference in its entirety.

The process at 512 derives hypothesized etiological explanations for the likelihood differences among the patient groups in each collection. For example, to develop an etiological explanation for the likelihood difference between a pair of patient groups, the system user first obtains the distinguishing likelihood variables from the system (e.g., as described above with reference to 504) and identifies the likelihood factors from which the distinguishing likelihood variables derive. The system user may then access clinical subject matter expertise and other clinical knowledge (e.g., see 508, 510) to relate the differences in distinguishing likelihood variable values to physiological processes associated with the likelihood factors and the outcome of interest. The resulting explanation would identify hypothesized physiological processes that are responsible for the difference in outcome likelihood between the two patient groups.

Thus, for example, the process at 512 may derive hypothesized etiological explanations for why one or more patient groups have higher likelihood of an adverse outcome of interest when compared to other defined patient groups. The output of the process at 512 is data at 514 that defines selected patient group collections with etiological explanations for likelihood differences within each collection.

Referring to FIG. 4 and FIG. 5 generally, the patient groups and hypothesized etiological explanations may be defined for the specific purpose of identifying clinical interventions that have the potential to lower the likelihood of the adverse health outcome of interest or increase the likelihood of a favorable health outcome of interest.

In alternative configurations, it may be more desirable to measure consequence rather than likelihood. Here, the component 500 of a progression analytics system may be provided, where the predicted outcome likelihoods, likelihood differences, likelihood factors etc., are replaced with predicted outcome consequence, consequence differences, consequence factors etc.

Clinical Interventions:

According to aspects of the present invention, the progression analytics system provides a GUI that enables a system user to identify clinical interventions intended to modify or prevent select physiological processes.

Figure 6:
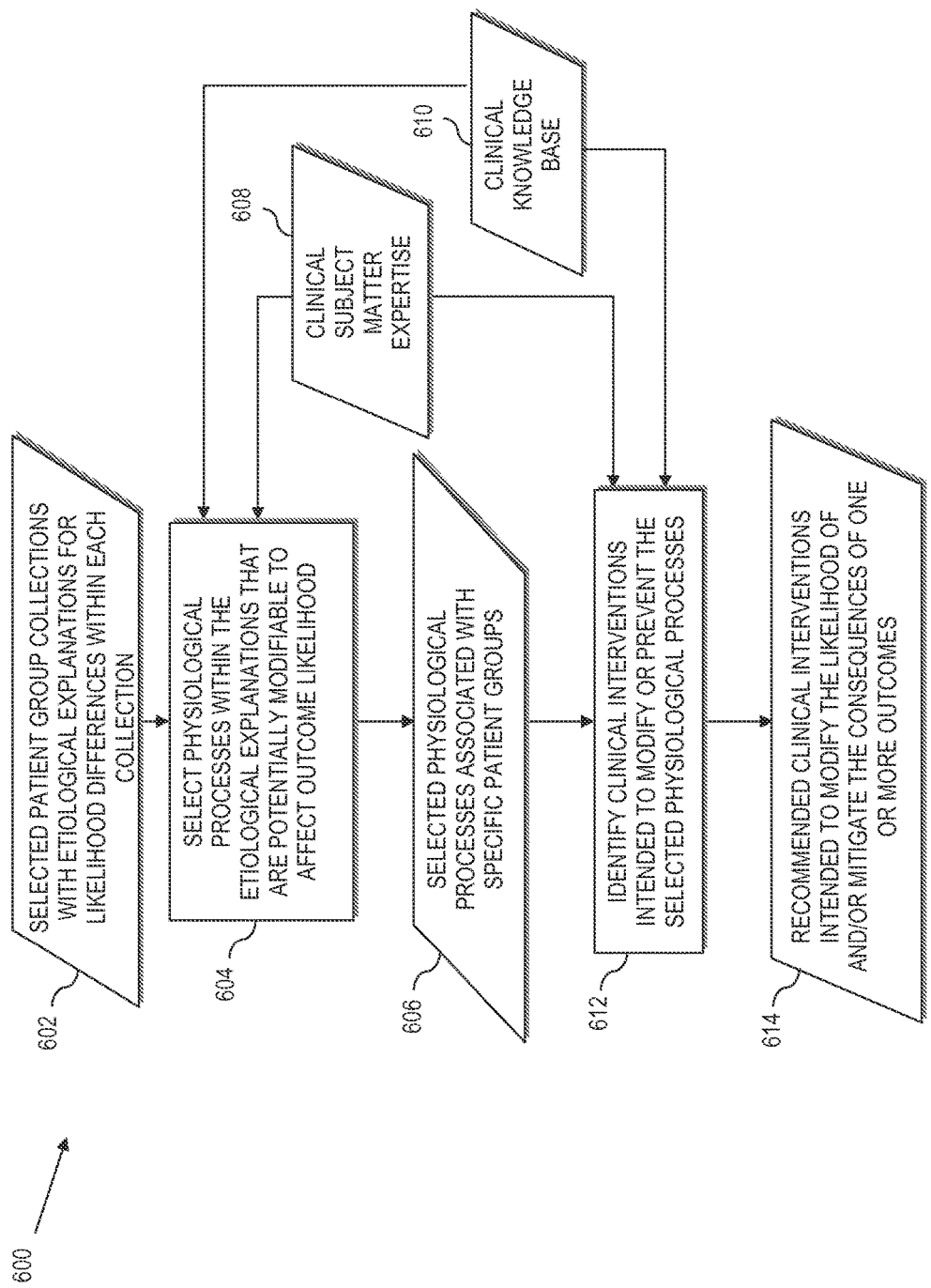
FIG. 6 is a flow diagram illustrating an approach for recommending clinical interventions based upon etiological explanations for differences in corresponding patient groups, according to aspects of the present disclosure.

Referring to FIG. 6, a component 600 is provided for identifying clinical interventions. The identified clinical interventions may be based upon previously derived hypothesized etiological explanations for why one or more patient groups have different likelihood of the outcome of interest when compared to other defined patient groups. For instance, the hypothesized etiological explanations may comprise physiological process descriptions that hypothesize a causal relationship between the data patterns that define patient groups and the likelihood of occurrence of the outcome of interest for individual groups. Moreover, as noted with regard to 508 and 510, the hypothesized etiological explanations may be derived, at least in part, based on clinical subject matter expertise, based on the contents of a clinical knowledgebase, or based on a combination of the two.

The method at 600 starts with data at 602 that defines selected patient group collections with etiological explanations for likelihood differences within each collection. For instance, the data at 602 may comprise the data at 514 that is generated by the component 500 described with reference to FIG. 5. A process at 604 selects physiological processes within the etiological explanations that are potentially modifiable to change the likelihood of the outcome of interest.

For example, in an exemplary implementation, the component 600 or other interface associated with the progression analytics system presents to the user a series of patient group pairs along with hypothesized etiological explanations for the outcome likelihood differences between the groups in each pair where the hypothesized etiological explanations include hypothesized physiological processes that are responsible for the difference in outcome likelihood. The system user may then access clinical subject matter expertise and other clinical knowledge (see 608, 610) to identify the physiological processes having the greatest potential to be modified in a manner that either decreases the likelihood of an adverse outcome or increases the likelihood of a favorable outcome.

The process at 604 outputs data at 606 that represents selected physiological processes associated with specific patient groups. As illustrated, the process at 604 may include inputs from other sources, including data at 608 corresponding to clinical subject matter expertise, data at 610 corresponding to data extracted from a clinical knowledgebase, combinations thereof, etc. The clinical knowledgebase 610 is an information repository such as the clinical knowledgebase 510 described with reference to FIG. 5. A process at 612 receives as input, the data at 606 representing the selected physiological processes. The process at 612 may also include inputs from other sources, including data at 608 corresponding to clinical subject matter expertise, data at 610 corresponding to data extracted from a clinical knowledgebase, combinations thereof, etc. The process at 612 identifies clinical interventions intended to modify or prevent the selected physiological processes. For example, based on a list of physiological processes for which modification has the potential to improve patient outcomes, the system user could access clinical subject matter expertise and other clinical knowledge to identify clinical interventions, interventions that could be implemented in the clinical setting, directed to modify the physiological processes with a result that either decreases the likelihood of an adverse outcome or increases the likelihood of a favorable outcome. The output of the process at 612 is data at 614 that defines recommended clinical interventions for specific patient groups.

If the outcome of interest is an adverse outcome, the recommendations of clinical interventions for one or more patient groups may be intended to decrease the likelihood of the adverse health outcome, reduce the consequences of the adverse health outcome, or both. In this regard, the clinical interventions may be identified that are directed to prevent patients from entering higher-likelihood patient groups, prevent patients from entering higher-consequence patient groups, lower the likelihood of the adverse outcome for patients in higher-likelihood patient groups, lower the consequences of the adverse outcome for patients in higher-consequence patient groups, or any combination of the foregoing, etc.

If the outcome of interest is a favorable outcome, the recommendations of clinical interventions for one or more patient groups may be intended to increase the likelihood of the favorable health outcome, increase the consequences of the favorable health outcome, or both. In this regard, the clinical interventions may be intended to assist patients in entering higher-likelihood patient groups, assist patients in entering higher-consequence patient groups, increase the likelihood of the favorable outcome for patients in lower-likelihood patient groups, increase the consequences of the favorable outcome for patients in lower-consequence patient groups, or any combination of the foregoing, etc.

As noted with regard to 608, 610, the clinical interventions may be identified based on clinical subject matter expertise, based on the contents of a clinical knowledgebase, or based on a combination of the two.

In alternative configurations, it may be more desirable to measure consequence rather than likelihood. Here, the component 600 of a progression analytics system may be provided, where the likelihood differences etc., are replaced with consequence differences, etc. In another example, where the measure of interest is risk, the likelihood differences, etc., are replaced with risk differences, etc. Other measures may also be utilized, e.g., which integrate, blend or otherwise strike a balance between likelihood and consequence.

Simplified Example to Explain Certain Concepts Herein

As noted in greater detail herein, insights into a patient-care related outcome of interest are identified by extracting electronic clinical data associated with historical healthcare encounters for a plurality of patients, where the plurality of patients are selected for the evaluation of an outcome of interest.

Take as an example, an adverse outcome of interest such as acute kidney injury (AKI). The systems and methods herein are utilized to identify likelihood variables (e.g., 308, 404) that have a clinical and/or statistical significance to AKI. Assume for this simplified example that three likelihood variables are identified, such as urinary output rate, respiratory rate, and serum creatinine concentration.

The method then defines patient groups among the plurality of patients, where each patient group is defined by grouping together those patients having a similar data pattern present in the extracted electronic clinical data. To implement this, the method first defines "data patterns". Here, the nature of the likelihood variables, the precision at which the likelihood of an adverse outcome can be computed, and other like considerations will decide how the data patterns are defined. For instance, in the present example, a simplified data pattern is defined by transforming the likelihood variables into discrete measures. The measures may be utilized to define one or more states for the likelihood variables, e.g., by defining ranges, groupings, orders, etc. For instance, in the simplified example, each measure represents a binary expression of a corresponding likelihood variable.

By way of example, the likelihood variable "urinary output rate" is transformed into a "high urinary output rate" measure, represented as a binary. If a particular patient is classified as having a high urinary output rate (e.g., by comparing the value corresponding to the patient's urinary output rate to a threshold), the high urinary output measure is Yes, represented by a data value 1.

Analogously, the likelihood variable "respiratory rate" is transformed into a "high respiratory rate" measure, represented as a binary. If a particular patient is classified as having a high respiratory rate (e.g., by comparing the value corresponding to the patient's respiratory rate to a threshold), the high respiratory rate measure is Yes, represented by a data value 1.

Likewise, the likelihood variable "serum creatinine concentration" is transformed into a "low serum creatinine concentration", represented as a binary. If a particular patient is classified as having a low serum creatinine concentration (e.g., by comparing the value corresponding to the patient's serum creatinine concentration to a threshold), the low serum creatinine concentration measure is Yes, represented by a data value 1.

Notably, this approach simplifies the analysis considerably, because 3 binary values can create up to eight groups. For each unique group, the method predicts the outcome likelihood as described in greater detail herein, producing predicted outcome likelihoods for each group.

As noted in greater detail herein, since the data used to select the patient groups is retrospective data, the patient data for the members of each group may indicate whether the patient did, or did not actually suffer the adverse outcome of interest, AKI in this example. As such, the method has an opportunity to compare the predicted outcome likelihood for each group with the actual likelihood of the adverse outcome for that group. Where such information is available, the method may compare the predicted likelihood value with the computed actual likelihood value for each group. If there is a strong correlation between the predicted outcome likelihood and the computed actual outcome likelihood, then there is a strong confidence in the outcome likelihood model. If the comparison of the predicted outcome likelihood to the computed actual outcome likelihood is too unfavorable, the method may iterate back, e.g., to select new likelihood variables, to alter the definitions of the measures, e.g., to be more granular, etc.

Assuming that the predicted outcome likelihood correlates well to an actual outcome likelihood for each group, the method next focuses on differences between groups, e.g., based upon their predicted outcome likelihood. For instance, keeping with the above-example, assume that the following computations are realized:

Patient group A has a high urinary output rate measure of Yes, a high respiratory rate measure of No and a low serum creatinine concentration measure of Yes, with a calculated predicted outcome likelihood of 3%.

Patient group B has a high urinary output rate measure of Yes, a high respiratory rate measure of Yes and a low serum creatinine concentration measure of Yes, with a calculated predicted outcome likelihood of 31%.

Comparing Patient group A to Patient group B, the only difference between them is the High respiratory rate. However, the predicted outcome likelihood for Group B is an order of magnitude higher than the predicted outcome likelihood for group A. As such, the method derives hypothesized etiological explanations for why a member of Patient group B has a higher likelihood of the adverse outcome of interest when compared to a member of Patient group A by focusing on the High respiratory rate of the patients in the Patient group B. For instance, a focused evaluation can attempt to ascertain one or more physiological processes that potentially explain why the patients in Group B with high respiratory rates have a much higher likelihood of AKI. By understanding the physiological processes leading to AKI, the method can identify clinical interventions for patient Group B (type patients) where the interventions are intended to decrease the likelihood of AKI, reduce the consequences of AKI or both by preventing future patients that would otherwise be classified in patient Group B from developing a high respiratory rate or preventing patients in patient group B from experiencing AKI.

The above example is for illustration and clarity of explanation of the concepts herein. In practice, there may be more than three likelihood variables associated with an outcome of interest. Moreover, each likelihood variable need not be expressed as a measure that is binary. Rather, the resolution of each likelihood variable may be determined based upon the number of variations in actual value of patients in the groups. Still further, one or more of the likelihood variables may be represented by a complex structure, such as a dynamic definition, one that includes temporal changes, and interaction among likelihood variables, a temporal ordering of events, etc.

Figure 7:
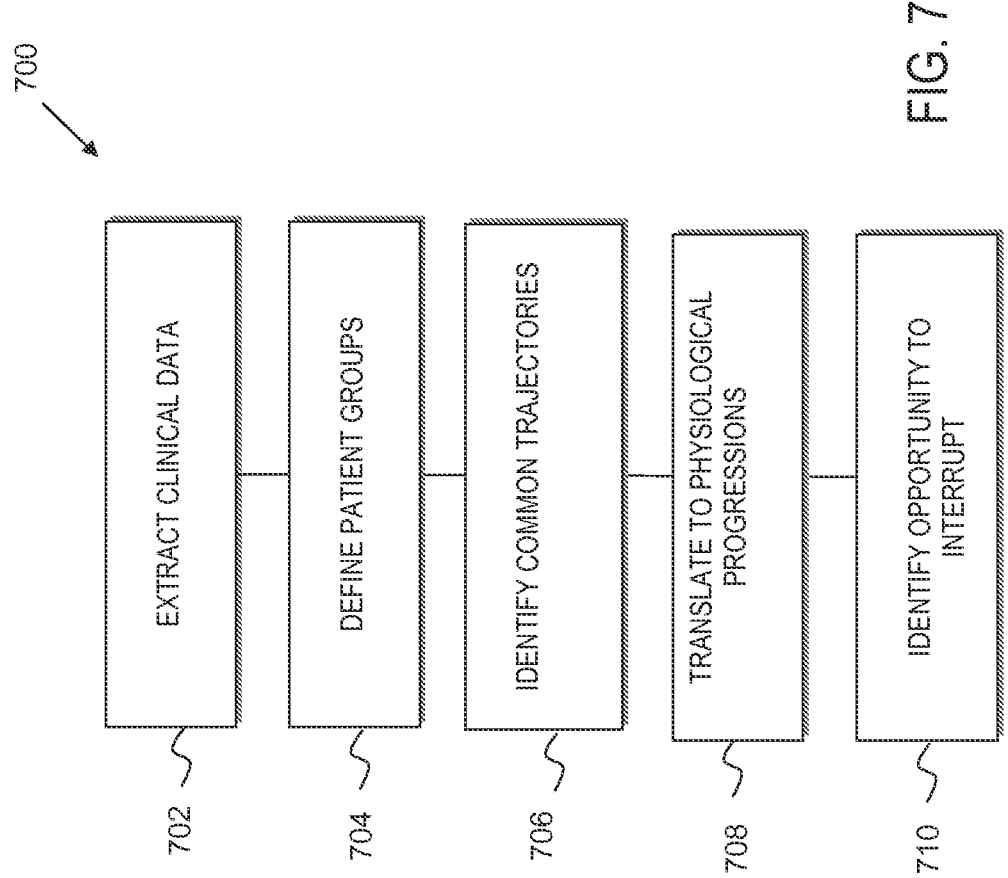
FIG. 7 is a flow chart of an exemplary flow within a progression analytics system that comprises defining patient groups, characterizing each group with a common care element trajectory, translating trajectories into hypothesized physiological progressions, and identifying opportunities to interrupt certain physiological progressions according to aspects of the present disclosure.

Progression Identification Using Trajectories:

Referring to FIG. 7, a method is provided for identifying physiological progressions, according to aspects of the present disclosure. The method comprises extracting, at 702, electronic clinical data associated with patients under evaluation. The extraction at 702 is analogous to the extraction at 202 described with reference to FIG. 2. As such, the discussion with regard to extracting electronic clinical data, as described with reference to the preceding figures, may be utilized for the extraction at 702.

The method comprises defining at 704, patient groups. The defining of patient groups at 704 is largely analogous to defining patent groups at 204 described with reference to FIG. 2. As such, the discussion with regard to defining patient groups, as described with reference to the preceding figures, may be utilized for defining the patient groups at 704. However, defining patient groups at 704 also includes generating patient groups based upon similar temporal, static, etc., data patterns extracted from the electronic clinical data.

In an illustrative example, a data pattern may be employed to define patient groups that comprise defining a pattern across a time history of changes in the physiological state of patients, occurrences of events that the patients experience, or both. In as yet another example, the variables that are used to define the data patterns need not be all temporal. Rather, in illustrative implementations, the data patterns employed to define patient groups include both non-temporal and temporal data patterns.

In this regard, the method 700 also comprises identifying a common trajectory associated with at least one defined patient group at 706 where the trajectories represent values of static variables and data patterns across a time history of changes in the physiological state of patients, occurrences of events that patients experience, or a combination of states and events over time. For instance, the extracted electronic clinical data and the constructed (likelihood, consequence) model can be utilized with data processing techniques that stratify and segment or cluster patients into patient groups that may be characterized by care element trajectories. These care element trajectories represent data patterns across a time-limited history of changes in the physiological state of patients, occurrences of events that patients experience, or a combination of physiological states and events over time.

Also, the method 700 comprises translating the common trajectory to a physiological progression at 708 where the physiological progression is a time-sequenced set of physiological processes that provide a hypothetical etiological explanation for why members of the patient group may experience an outcome of interest. The method 700 further comprises identifying opportunities to interrupt one or more of the physiological processes involved in one or more of the physiological progressions for the purpose of reducing the likelihood of an adverse outcome, mitigating the consequences of an adverse outcome, or both.

Thus, progressions are constructed that characterize sequences of conditions that patients progress through on a path to an outcome (either favorable or unfavorable). The progressions are constructed using common trajectories defined by patient groups, where the patient groups are generated based upon similar (temporal, non-temporal, or a combination thereof) data patterns, of patients within the group.

Moreover, a trajectory is identified, which is associated with at least one defined patient group. For instance, the patient groups can be identified by analyzing the electronic clinical data over time and clustering or otherwise segmenting the electronic clinical data. The electronic clinical data is clustered or segmented so as to define groups of patients that have similar data patterns. From the clusters or segments of data associated with the patient groups, trajectories can be extracted. A trajectory represents a data pattern and can be mapped to an implied condition pattern. The implied condition pattern may correspond to a hypothesized physiological progression. Thus, the trajectory that a patient (or patient group) follows, may be mapped to a physiological progression.

In this regard, more than one trajectory may be derived. Also, a trajectory may be determined based upon a statistical analysis of the clustered or segmented data points representing the patients belonging to a group. For instance, the trajectory may pass through the centroid of the patients belonging to a particular group.

Aspects of the present disclosure present an opportunity to compare and otherwise evaluate trajectories, and to correlate trajectories with physiological progressions. The identification of a physiological progression presents an opportunity to intervene and alter the progression using interventions that have been established as capable of lowering the likelihood of an adverse outcome.

As another illustrative example, the patterns can be used as a tool to mitigate the likelihood that a patient remains on a trajectory that ultimately leads to an adverse outcome. By analyzing the physiological progressions, a clinician can identify opportunities to adjust patient care, e.g., by amending patient care protocols, etc.

As an example, consider acute kidney injury (AKI). After analyzing the electronic clinical data as set out above, the data may suggest that there are six ways (six trajectories that each identify a corresponding physiological progression) that can progress to AKI. It may turn out that two of the six identified physiological progressions can be eliminated with a systematic protocol change for the treatment of patients. It may further turn out that the likelihood of AKI along two of the six identified physiological progressions can be greatly reduced with a systematic protocol change for the treatment of patients. It may still further turn out that two of the six identified physiological progressions cannot be affected. In this illustrative, but non-limiting example, overall patient care is improved through the systematic changes in care protocols learned through the retrospective analysis of electronic clinical data.

Moreover, the systematic protocol changes, e.g., new, modified or eliminated intervention that is being considered by a clinician can be verified for its effectiveness in certain circumstances. For instance, by changing a protocol for care, the system user changes the trajectory that patient is following. As such, the system user can go back to the clustered or otherwise segmented data and identify new groups of patients that follow a trajectory corresponding to the intervention that is being considered. If the patients in that new group have a lower likelihood, the system user obtains confidence in the proposed change. As another example, the hospital system can implement the change to an intervention for new patients. Over time, patient data will be collected for patients that follow the new protocol, which will generate a patient group that can be evaluated to determine whether the new group has a weaker trajectory towards the adverse outcome.

Trajectory to Physiological Progression Translation

Variables that are observable represent a chance to evaluate underlying conditions. This enables a clinician to surmise information regarding a patient's health. In this regard, a clinician may or may not be able to observe whether the patient actually has a corresponding condition. For instance, even where a clinician diagnoses a condition, there may be insufficient information available to properly ascertain whether the patient actually has the condition.

Aspects of the present disclosure herein define physiological progressions, e.g., sequences of conditions/events/processes or other physiological characteristics that a patient progresses through on a path to an outcome (either adverse or favorable). The clinician may not be able to observe the physiological progression, but the clinician can see the outward effect of the physiological progression in the observed (likelihood, consequence) variables.

According to aspects of the present disclosure herein, a trajectory is defined, based upon an analysis, e.g., clustering or otherwise segmenting electronic clinical data patterns including patterns over time. A trajectory corresponds to a path, e.g., a vector or other measure that allows patient data to be analyzed, clustered and otherwise evaluated for trend analysis, similarity matching, etc. The system as described more fully herein, can evaluate historical electronic clinical data where outcome information is available and compute for each patient or patient group in the historical information, a trajectory.

By way of illustration, a historical group of patients may be evaluated to identify an observable trajectory where all of the patients follow the same temporal data pattern leading to an adverse outcome, such as acute kidney injury (AKI). Here, the trajectory is more than just a single event defining the adverse outcome. Rather, the trajectory includes a time history of measures, e.g., symptoms, conditions, events or other observable aspects. However, this trajectory can be discerned from patterns in clustered or segmented patient data as described more fully herein.

Thus, electronic clinical data can be evaluated. A system user can study various clusters/segments/groups of data to understand the key drivers (trajectories) that translate to physiological progressions that ultimately lead to an adverse outcome for those patients on that trajectory. The system user can thus set out to evaluate what can be changed in patient care to avoid certain trajectories, to detour patients from certain trajectories, to reduce likelihood if a patient is on a certain trajectory, etc.

Miscellaneous Considerations:

With reference to the FIGURES generally, as noted in greater detail herein, care element progressions are identified by extracting electronic clinical data associated with patients under evaluation. According to aspects of the present disclosure, the information that comprises the electronic clinical data (see for example, trajectory data included in the electronic clinical data) can be derived from the data types corresponding to electronic patient data, the (likelihood, consequence) variables, the outcome (likelihood, consequence) models, attributions, etc.

In this regard, the electronic clinical data may be logically organized in a temporal manner. For example, a time sequence of data variables can be created from the electronic clinical data where the state of a value for each variable is represented for that time. In this regard, the intervals may be event based or otherwise event driven. Conceptually, this can be thought of as a table where the various "types" of electronic clinical data define the columnar fields used for analysis, and a time sequence defines the rows of the table. The intervals (rows) may be determined based upon events that cause the status of a variable to change.

For instance, in an example implementation, the creation of a new row is event-based in that a new row is created any time new information becomes available for the patient. Each row is then date and time stamped with the time that the new information became available. Information for other variables is carried forward from the previous record unless it has expired. Thus, the creation of new records is event-based but the records represent a time-stamped temporal series of data. Thus, the values of the records are the state/value of each electronic clinical data type at a given time, and accordingly, each record represents a snapshot in time. Alternatively, the above can be conceptualized as an array of data elements extended as a vector that represents time. This organization facilitates retrospective temporal analysis of the electronic clinical data.

The above importance of temporally oriented data characterization notwithstanding, changes in the values or states of variables may be important to defining trajectories regardless of time at which the changes occur. As stated elsewhere within, the values of static variables may be important as well. Thus trajectories will have static elements, time-independent elements and temporally oriented elements.

Moreover, electronic clinical data can be derived from a subset of the above data sources, e.g., by selecting key data types, by performing data synthesis, data manipulation, etc. For instance, it may be desirable to filter the available electronic clinical data down to the key variables that are related to an outcome of interest.

Various aspects of the present invention are directed to identifying insights related to the occurrence of an outcome of interest. An example is an adverse health outcome such as acute kidney injury. However, the adverse outcome of interest may be defined to be the occurrence of one or more of a set of adverse health outcomes, thus allowing the systems and methods herein to be scaled to accommodate a wide range of health analytics.

Moreover, the systems and methods described herein may obtain electronic clinical data for new patients. Then using the systems and methods set out herein, the new patients may be assigned to previously-defined patient groups to identify recommended clinical interventions for the new patients based on previously-identified interventions for the previously-defined patient groups. Here, tracking the outcomes experienced by the new patients after recommended clinical interventions have been implemented may be used, for instance, for the purpose of assessing the value of the recommendations in lowering the likelihood of one or more adverse health outcomes of interest.

Root Cause Analysis:

According to still further aspects of the present disclosure, retrospective systemic root cause analysis is utilized to support clinical analysis and may even be used to affect policy decision making Basically, the root cause analysis uses retrospection of a population of data to draw conclusions across the population as to the likely root cause(s) that lead to the eventual adverse outcomes identified within the patient data. As such, clinical policy decisions can be made, to respond to detected patterns.

Example Computer Implementation

Figure 8:
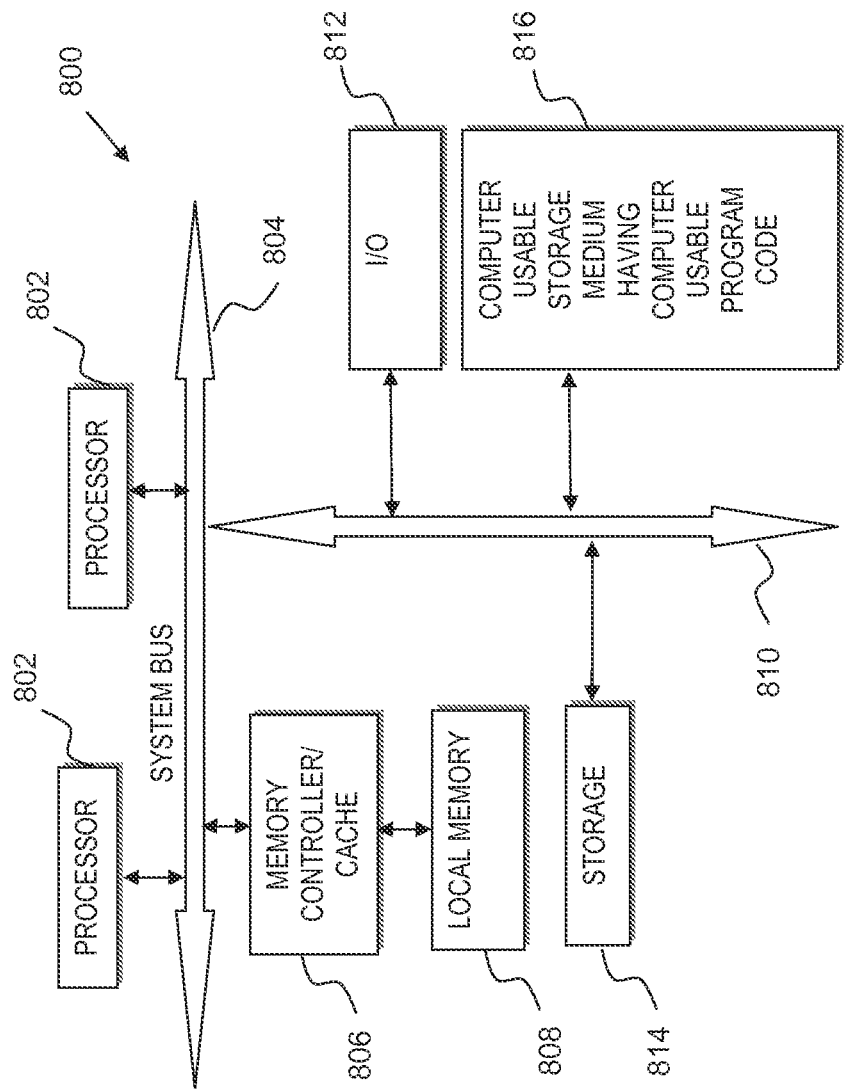
FIG. 8 is a block diagram of an exemplary computer system, which may be utilized for implementing one or more components of FIGS. 1-7, according to aspects of the present disclosure.

Referring to FIG. 8, a block diagram of a data processing system is depicted in accordance with the present disclosure. Data processing system 800 may comprise one or more processors 802 connected to system bus 804. Also connected to system bus 804 is memory controller/cache 806, which provides an interface to local memory 808. An I/O bus 810 is connected to the system bus 804 and provides an interface to I/O devices 812, such as input output devices (I/O devices), storage, network adapters, graphic adapters, etc.

Also connected to the I/O bus 810 may be devices such as one or more storage devices 814 and a computer usable storage medium 816 having computer usable program code embodied thereon. The computer usable program code may be executed, e.g., by the processor(s) 802 to implement any aspect of the present disclosure, for example, to implement any aspect of any of the methods, processes and/or system components illustrated in FIGS. 1-7.

The present invention may be a system, a method, and/or a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device, e.g., the system described with reference to FIG. 8. Thus, a computer readable storage medium, as used herein, is not to be construed as being transitory signals per se, such as radio waves or other freely propagating electromagnetic waves through a transmission media.

Exemplary and non-limiting structures for implementing a computer readable storage medium include a portable computer diskette, a hard disk, a random access memory (RAM), Flash memory, a read-only memory (ROM), a portable compact disc read-only memory (CD-ROM), digital video disk (DVD), an optical storage device, a magnetic storage device, or any suitable combination of the foregoing.

Aspects of the present disclosure are described herein with reference to flowchart illustrations and/or block diagrams of methods, apparatus (systems) and computer program products according to embodiments of the disclosure. Each block of the flowchart illustrations and/or block diagrams, and combinations of blocks in the flowchart illustrations and/or block diagrams, can be implemented by computer program instructions, such that the instructions, which execute via the processor of the computer or other programmable data processing apparatus, create means for implementing the functions/acts specified in the flowchart and/or block diagram block or blocks.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

Each block in the flowchart or block diagrams of the FIGURES herein, may represent a module, segment, or portion of code, which comprises one or more executable instructions for implementing the specified logical function(s). However, the functions noted in the block may occur out of the order noted in the figures. For example, two blocks shown in succession may, in fact, be executed substantially concurrently, or the blocks may sometimes be executed in the reverse order, depending upon the functionality involved.

The terminology used herein is for the purpose of describing particular embodiments only and is not intended to be limiting of the disclosure. As used herein, the singular forms "a," "an," and "the" are intended to include the plural forms as well, unless the context clearly indicates otherwise. Further, the terms "comprises" and "comprising," when used in this specification, specify the presence of stated features, steps, operations, elements, and/or components, but do not preclude the presence or addition of one or more other features, steps, operations, elements, components, and/or groups thereof.

The corresponding structures, materials, acts, and equivalents of any means or step plus function elements in the claims below are intended to include any disclosed structure, material, or act for performing the function in combination with other claimed elements as specifically claimed. The description of the present disclosure has been presented for purposes of illustration and description, but is not intended to be exhaustive or limited to the disclosure in the form disclosed. Many modifications and variations will be apparent to those of ordinary skill in the art without departing from the scope and spirit of the disclosure. The aspects of the disclosure herein were chosen and described in order to best explain the principles of the disclosure and the practical application, and to enable others of ordinary skill in the art to understand the disclosure with various modifications as are suited to the particular use contemplated.

Having thus described the disclosure of the present application in detail and by reference to embodiments thereof, it will be apparent that modifications and variations are possible without departing from the scope of the disclosure defined in the appended claims.

What is claimed is:

1. A computer-implemented method of evaluating outcomes, comprising:

identifying a patient care-related outcome of interest;

extracting electronic clinical data associated with historical healthcare encounters for a plurality of patients, by:
    including in the plurality of patients, a first subset of patients that experienced the outcome of interest; and
    including in the plurality of patients, a second subset of patients that did not experience the outcome of interest;

deriving at least one model based upon model variables that have a clinical and/or statistical significance to the outcome of interest the at least one model selected from:
    an outcome likelihood model that estimates the likelihood of the outcome of interest using a group of likelihood variables, and
    a consequence likelihood model that estimates consequences of the outcome of interest using a group of consequence variables;

determining patient groups among the plurality of patients for which electronic clinical data is extracted, with the aid of a computer processor that executes a program, by:
    defining each patient group by grouping together those patients having a similar data pattern present in their corresponding extracted electronic clinical data based upon at least one model variable: and
    selecting the data patterns such that the defined patient groups differentiate from one another in terms of a likelihood of the outcome of interest, consequences associated with the outcome of interest or both based upon clinical data associated with a value of the at least one model variable;

deriving a hypothesized etiological explanation for why one or more patient groups have different likelihoods of the outcome of interest, consequences associated with the outcome of interest or both, when compared to other defined patient groups, by comparing defined patient groups and identifying different likelihoods of the outcome of interest;

identifying at least one physiological process associated with the derived hypothesized etiological explanation;

outputting a clinical intervention based upon the identified physiological process;

selecting the clinical intervention for a select patient group wherein the identified clinical intervention is directed to decrease the likelihood of the adverse outcome of interest or decrease the consequences of the adverse outcome of interest, or both, for the select patient group; and verifying the effectiveness of the selected clinical intervention by:
    generating a patient group that follows a trajectory corresponding to the selected clinical intervention; and
    determining a likelihood of the outcome of interest for the generated patient group; and modifying the selected clinical intervention based upon the determined likelihood of outcome of interest for the generated patient group.

2. The method of claim 1, wherein selecting the clinical intervention comprises selecting the clinical intervention that is directed to prevent patients from entering higher-likelihood patient groups, prevent patients from entering higher-consequence patient groups, lower the likelihood of the adverse outcome for patients in higher-likelihood patient groups, lower the consequences of the adverse outcome for patients in higher-consequence patient groups, or any combination of the foregoing.

3. The method of claim 1, wherein identifying a patient care-related outcome of interest comprises selecting a favorable outcome of interest, and further comprising:
selecting the clinical intervention for a select patient group wherein the clinical intervention is directed to increase the likelihood of the favorable outcome of interest or increase the consequences of the favorable outcome of interest, or both, for the select patient group.

4. The method of claim 3, wherein selecting the clinical intervention comprises selecting the clinical intervention to assist patients in entering higher-likelihood patient groups, assist patients in entering higher-consequence patient groups, increase the likelihood of the favorable outcome for patients in lower-likelihood patient groups, increase the consequences of the favorable outcome for patients in lower-consequence patient groups, or any combination of the foregoing.

5. The method according to claim 1, wherein defining each patient group comprises creating at least one patient group as including at least one patient from the first subset of patients and at least one patient from the second subset of patients.

6. The method according to claim 1, wherein extracting electronic clinical data comprises extracting likelihood variables or consequence variables or both, wherein the likelihood variables define variables associated with a patient's likelihood of having the outcome of interest and consequence variables define variables associated with a patient's consequences associated with the outcome of interest.

7. The method of claim 6, wherein:
extracting likelihood variables comprises generating the likelihood variables as a result of reconciliation of likelihood factors identified by outcome-specific etiological models with available patient data; and
extracting consequence variables comprises generating the consequence variables as a result of reconciliation of consequence factors identified by outcome-specific etiological models with available patient data.

8. The method according to claim 6, wherein grouping together those patients having a similar data pattern present in their corresponding extracted electronic clinical data comprises defining similar data patterns based upon the data values of a subset of the likelihood variables, consequence variables or both, such that the patient groups are defined in terms of variables and not in terms of whether or not the patient has experienced the outcome of interest.

9. The method according to claim 8 further comprising:
converting the subset of the likelihood variables, consequence variables or both, into discrete measures having a fixed number of value options;
wherein grouping together those patients having a similar data pattern comprise grouping together those patients having the same data values associated with the discrete measures.

10. The method according to claim 1, wherein grouping together those patients having a similar data pattern present in their corresponding extracted electronic clinical data comprises grouping together those patients having a data pattern that includes both non-temporal and temporal data patterns.

11. The method according to claim 1, wherein grouping together those patients having a similar data pattern present in their corresponding extracted electronic clinical data comprises identifying a common trajectory associated with at least one defined patient group where the trajectory represents a data pattern across a time history of changes in the physiological state of patients, occurrences of events that patients experience, or a combination of states and events over time.

12. The method according to claim 1, wherein grouping together those patients having a similar data pattern present in their corresponding extracted electronic clinical data comprises defining a data pattern by defining values of one or more static variables that do not change during the course of a hospital encounter and/or defining a pattern across a time history of changes in the physiological state of patients, occurrences of events that the patients experience, or both.

13. The method according to claim 1, wherein defining each patient group comprises developing an outcome likelihood scoring algorithm that characterizes the likelihood of the outcome of interest as a function of likelihood variables derived from extracted electronic clinical data and defining the patient groups based on data patterns in the likelihood variables employed in the scoring algorithm.

14. The method of claim 13, further comprising configuring the outcome likelihood scoring algorithm to define the likelihood of the outcome of interest in terms of baseline and dynamic likelihoods.

15. The method according to claim 1, wherein defining each patient group comprises developing an outcome consequence scoring algorithm that characterizes the consequences associated with the outcome of interest as a function of consequence variables derived from extracted electronic clinical data and defining the patient groups based on data patterns in the consequence variables employed in the scoring algorithm.

16. The method according to claim 1, wherein defining each patient group comprises clustering or segmenting the extracted electronic clinical data and defining a patient group for each data cluster or segment.

17. The method according to claim 1, wherein deriving a hypothesized etiological explanation comprises deriving physiological process descriptions that hypothesize a causal relationship between the data patterns that define patient groups and the likelihood of occurrence of and/or consequences associated with the outcome of interest for individual groups.

18. The method according to claim 1, wherein deriving a hypothesized etiological explanation comprises deriving the hypothesized etiological explanations based on clinical subject matter expertise, based on the contents of a clinical knowledgebase, or by a combination of the two.

19. The method according to claim 1, further comprising:
identifying the clinical intervention for a select patient group wherein the clinical intervention is identified based on clinical subject matter expertise, based on the contents of a clinical knowledgebase, or based on a combination of the two.

20. The method according to claim 1, further comprising:
obtaining electronic clinical data for new patients;
assigning the new patients to previously-defined patient groups; and recommending one or more clinical interventions for the new patients based on previously-identified interventions for the previously-defined patient groups.

21. The method of claim 20, further comprising:
applying the method iteratively over time to achieve continuous improvement in patient care relative to the outcome of interest.

22. The method of claim 20 further comprising:
tracking the outcomes experienced by the new patients after clinical interventions have been recommended for the purpose of assessing the value of the recommendations in improving patient care relative to the outcome of interest.

23. An apparatus, comprising:
a processor coupled to a memory, wherein the processor is programmed to identify insights related to outcomes by executing program code to:
identify a patient care-related outcome of interest;
extract electronic clinical data associated with historical healthcare encounters for a plurality of patients, wherein:
  the plurality of patients include a first subset of patients that experienced the outcome of interest; and
  the plurality of patients include a second subset of patients that did not experience the outcome of interest;
derive at least one model based upon model variables that have a clinical and/or statistical significance to the outcome of interest the at least one model selected from:
  an outcome likelihood model that estimates the likelihood of the outcome of interest using a group of likelihood variables, and
  a consequence likelihood model that estimates consequences of the outcome of interest using a group of consequence variables;
define patient groups among the plurality of patients, wherein:
  each patient group is defined by grouping together those patients having a similar data pattern present in their corresponding extracted electronic clinical data based upon at least one model variable: and
  the data patterns are selected such that the defined patient groups differentiate from one another in terms of a likelihood of the outcome of interest, consequences associated with the outcome of interest or both based upon clinical data associated with a value of the at least one model variable;
provide an interface for a user to derive hypothesized etiological explanations for why one or more patient groups have different likelihoods of the outcome of interest, consequences associated with the outcome of interest or both, when compared to other defined patient groups;
identify at least one physiological process associated with the derived hypothesized etiological explanation;
output a clinical intervention based upon the identified physiological process;
select the clinical intervention for a select patient group wherein the identified clinical intervention is directed to decrease the likelihood of the adverse outcome of interest or decrease the consequences of the adverse outcome of interest, or both, for the select patient group; and
verify the effectiveness of the selected clinical intervention by:
  generating a patient group that follows a trajectory corresponding to the selected clinical intervention; and
  determining a likelihood of the outcome of interest for the generated patient group; and
modify the selected clinical intervention based upon the determined likelihood of outcome of interest for the generated patient group.

* * * * *